US011147633B2

(12) United States Patent
Ye

(10) Patent No.: US 11,147,633 B2
(45) Date of Patent: Oct. 19, 2021

(54) INSTRUMENT IMAGE RELIABILITY SYSTEMS AND METHODS

(71) Applicant: Auris Health, Inc., Redwood City, CA (US)

(72) Inventor: Menglong Ye, Mountain View, CA (US)

(73) Assignee: Auris Health, Inc., Redwood City, CA (US)

(*) Notice: Subject to any disclaimer, the term of this patent is extended or adjusted under 35 U.S.C. 154(b) by 0 days.

(21) Appl. No.: 17/005,165

(22) Filed: Aug. 27, 2020

(65) Prior Publication Data

US 2021/0059765 A1   Mar. 4, 2021

Related U.S. Application Data

(60) Provisional application No. 62/894,601, filed on Aug. 30, 2019.

(51) Int. Cl.
*G06T 7/73* (2017.01)
*A61B 1/00* (2006.01)
(Continued)

(52) U.S. Cl.
CPC ............ *A61B 34/20* (2016.02); *A61B 1/0002* (2013.01); *A61B 1/05* (2013.01); *A61B 1/2676* (2013.01);
(Continued)

(58) Field of Classification Search
USPC ........................................................ 600/408
See application file for complete search history.

(56) References Cited

U.S. PATENT DOCUMENTS

| 4,745,908 A | 5/1988 | Wardle |
| 5,273,025 A | 12/1993 | Sakiyama et al. |

(Continued)

FOREIGN PATENT DOCUMENTS

| CN | 101147676 | 3/2008 |
| CN | 101222882 | 7/2008 |

(Continued)

OTHER PUBLICATIONS

Al-Ahmad et al., dated 2005, Early experience with a computerized robotically controlled catheter system, Journal of Interventional Cardiac Electrophysiology, 12:199-202.

(Continued)

*Primary Examiner* — Patricia I Young
(74) *Attorney, Agent, or Firm* — Chang & Hale LLP

(57) ABSTRACT

Described herein are systems and methods related to image management. A system may include an instrument that includes an elongate body and an imaging device. The elongate body can be configured to be inserted into a luminal network. The imaging device may be positioned at a distal tip of the elongate body. The system may receive from the imaging device one or more images captured when the elongate body is within the luminal network. For each of the images, the system may determine one or more metrics that are indicative of a reliability of an image for localization of the distal tip of the elongate body within the luminal network. The system may determine a reliability threshold value for each of the one or more metrics. The system can utilize the one or more images based on whether the one or more metrics meet corresponding reliability threshold values.

31 Claims, 25 Drawing Sheets

(51) Int. Cl.
    *A61B 1/05*       (2006.01)
    *A61B 1/267*     (2006.01)
    *A61B 5/00*       (2006.01)
    *G06K 9/46*       (2006.01)
    *G06K 9/62*       (2006.01)
    *A61B 34/20*     (2016.01)
    *A61B 10/00*     (2006.01)
    *A61B 10/02*     (2006.01)
    *A61B 34/30*     (2016.01)

(52) U.S. Cl.
    CPC .......... *A61B 5/7267* (2013.01); *G06K 9/4652* (2013.01); *G06K 9/4671* (2013.01); *G06K 9/6256* (2013.01); *G06K 9/6284* (2013.01); *G06T 7/73* (2017.01); *A61B 10/0233* (2013.01); *A61B 2034/2051* (2016.02); *A61B 2034/301* (2016.02); *A61B 2217/005* (2013.01); *A61B 2217/007* (2013.01)

(56) References Cited

U.S. PATENT DOCUMENTS

| | | |
|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Lahdesmaki |
| 6,665,554 B1 | 12/2003 | Charles |
| 6,690,963 B2 | 2/2004 | Ben-Haim |
| 6,690,964 B2 | 2/2004 | Beiger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Beiger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,697,972 B2 | 4/2010 | Verard |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,084,623 B2 | 7/2015 | Gomez et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,278,778 B2 | 5/2019 | State |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,492,741 B2 | 10/2019 | Walker et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,543,048 B2 | 1/2020 | Noonan et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |

(56) References Cited

U.S. PATENT DOCUMENTS

| | | |
|---|---|---|
| 10,779,898 B2 | 9/2020 | Hill |
| 10,786,329 B2 | 9/2020 | Schuh et al. |
| 10,786,432 B2 | 9/2020 | Jornitz et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu |
| 10,881,280 B2 | 1/2021 | Baez |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0015096 A1 | 1/2006 | Hauck et al. |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0147089 A1 | 6/2008 | Loh |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0221425 A1 | 9/2008 | Olson et al. |
| 2008/0243142 A1 | 10/2008 | Gildenberg |
| 2008/0262297 A1 | 10/2008 | Gilboa |
| 2008/0275349 A1 | 11/2008 | Halperin |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Sydora |
| 2010/0121139 A1 | 5/2010 | OuYang |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1 | 7/2011 | Higgins |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Holsing |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0120305 A1 | 5/2012 | Takahashi |
| 2012/0165656 A1 | 6/2012 | Montag |
| 2012/0172712 A1 | 7/2012 | Bar-Tal |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1 | 11/2012 | Chopra |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |

(56) References Cited

U.S. PATENT DOCUMENTS

| | | |
|---|---|---|
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0072192 A1 | 3/2014 | Reiner |
| 2014/0107390 A1 | 4/2014 | Brown |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0180063 A1 | 6/2014 | Zhao |
| 2014/0235943 A1 | 8/2014 | Paris |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0343416 A1 | 11/2014 | Panescu |
| 2014/0350391 A1 | 11/2014 | Prisco et al. |
| 2014/0357984 A1 | 12/2014 | Wallace et al. |
| 2014/0364739 A1 | 12/2014 | Liu |
| 2015/0051482 A1 | 2/2015 | Liu et al. |
| 2015/0054929 A1 | 2/2015 | Ito et al. |
| 2015/0057498 A1 | 2/2015 | Akimoto |
| 2015/0073266 A1 | 3/2015 | Brannan |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0008033 A1 | 1/2016 | Hawkins et al. |
| 2016/0111192 A1 | 4/2016 | Suzara |
| 2016/0128992 A1 | 5/2016 | Hudson |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0372743 A1 | 12/2016 | Cho et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe |
| 2017/0340241 A1 | 11/2017 | Yamada |
| 2017/0348067 A1 | 12/2017 | Krimsky |
| 2017/0360508 A1 | 12/2017 | Germain et al. |
| 2018/0025666 A1 | 1/2018 | Ho et al. |
| 2018/0055576 A1 | 3/2018 | Koyrakh |
| 2018/0055582 A1 | 3/2018 | Krimsky |
| 2018/0098690 A1 | 4/2018 | Iwaki |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0263714 A1 | 9/2018 | Kostrzewski |
| 2018/0279852 A1 | 10/2018 | Rafii-Tari et al. |
| 2018/0286108 A1 | 10/2018 | Hirakawa |
| 2018/0289431 A1 | 10/2018 | Draper et al. |
| 2018/0296281 A1* | 10/2018 | Yeung .................. G06K 9/6271 |
| 2018/0308232 A1 | 10/2018 | Gliner |
| 2018/0308247 A1 | 10/2018 | Gupta |
| 2018/0325499 A1 | 11/2018 | Landey et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0086349 A1 | 3/2019 | Nelson |
| 2019/0110839 A1 | 4/2019 | Rafii-Tari et al. |
| 2019/0110843 A1* | 4/2019 | Ummalaneni ......... A61G 13/04 |
| 2019/0151148 A1 | 4/2019 | Alvarez et al. |
| 2019/0125164 A1 | 5/2019 | Roelle et al. |
| 2019/0142519 A1 | 5/2019 | Siemionow et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0038123 A1 | 2/2020 | Graetzel |
| 2020/0039086 A1 | 2/2020 | Meyer |
| 2020/0046434 A1 | 2/2020 | Graetzel |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |

(56) References Cited

U.S. PATENT DOCUMENTS

| | | |
|---|---|---|
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |
| 2020/0405317 A1 | 12/2020 | Wallace |
| 2020/0405411 A1 | 12/2020 | Draper et al. |
| 2020/0405419 A1 | 12/2020 | Mao |
| 2020/0405420 A1 | 12/2020 | Purohit |
| 2020/0405423 A1 | 12/2020 | Schuh |
| 2020/0405424 A1 | 12/2020 | Schuh |
| 2020/0405434 A1 | 12/2020 | Schuh |
| 2020/0406002 A1 | 12/2020 | Romo |

FOREIGN PATENT DOCUMENTS

| | | |
|---|---|---|
| CN | 102316817 | 1/2012 |
| CN | 102458295 | 5/2012 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 104758066 | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3 025 630 | 6/2016 |
| KR | 10-2014-0009359 | 1/2014 |
| KR | 10-1713676 B1 | 3/2017 |
| RU | 2569699 C2 | 11/2015 |
| WO | WO 05/087128 | 9/2005 |
| WO | WO 06/051523 | 5/2006 |
| WO | WO 09/097461 | 6/2007 |
| WO | WO 15/089013 | 6/2015 |
| WO | WO 16/077419 | 5/2016 |
| WO | WO 16/203727 | 12/2016 |
| WO | WO 17/030916 | 2/2017 |
| WO | WO 17/036774 | 3/2017 |
| WO | WO 17/048194 | 3/2017 |
| WO | WO 17/066108 | 4/2017 |
| WO | WO 17/146890 | 8/2017 |
| WO | WO 17/167754 | 10/2017 |

OTHER PUBLICATIONS

Bell et al., 2014, Six DOF motion estimation for teleoperated flexible endoscopes using optical flow: a comparative study, IEEE International Conference on Robotics and Automation.
Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.
Fallavollita et al., 2010, Acquiring multiview C-arm images to assist cardiac ablation procedures, EURASIP Journal on Image and Video Processing, vol. 2010, Article ID 871408, pp. 1-10.
Gutierrez et al., Mar. 2008, A practical global distortion correction method for an image intensifier based x-ray fluoroscopy system, Med. Phys, 35(3):997-1007.
Haigron et al., 2004, Depth-map-based scene analysis for active navigation in virtual angioscopy, IEEE Transactions on Medical Imaging, 23(11):1380-1390.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Konen et al., 1998, The VN-project: endoscopic image processing for neurosurgery, Computer Aided Surgery, 3:1-6.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Marrouche et al., dated May 6, 2005, AB32-1, Preliminary human experience using a novel robotic catheter remote control, Heart Rhythm, 2(5):S63.
Mayo Clinic, Robotic Surgery, https://www.mayoclinic.org/tests-procedures/robotic-surgery/about/pac-20394974?p=1, downloaded from the internet on Jul. 12, 2018, 2 pp.
Mourgues et al., 2002, Flexible calibration of actuated stereoscopic endoscope for overlay in robot assisted surgery, International Conference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Oh et al., dated May 2005, p. 5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventional radiology suite, AJR, 189:W357-W364.
Reddy et al., May 2005, p. 1-53. Porcine pulmonary vein ablation using a novel robotic catheter control system and real-time integration of CT imaging with electroanatomical mapping, Hearth Rhythm, 2(5):S121.
Ren et al., 2011, Multisensor data fusion in an integrated tracking system for endoscopic surgery, IEEE Transactions on Information Technology in Biomedicine, 16(1):106-111.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813.

(56) References Cited

OTHER PUBLICATIONS

Shi et al., Sep. 14-18, 2014, Simultaneous catheter and environment modeling for trans-catheter aortic valve implantation, IEEE/RSJ International Conference on Intelligent Robots and Systems, pp. 2024-2029.

Slepian, dated 2010, Robotic Catheter Intervention: the Hansen Medical Sensei Robot Catheter System, PowerPoint presentation, 28 pp.

Solheim et al., May 14, 2009, Navigated resection of giant intracranial meningiomas based on intraoperative 3D ultrasound, Acta Neurochir, 151:1143-1151.

Solomon et al., Dec. 2000, Three-dimensional CT-Guided Bronchoscopy With a Real-Time Electromagnetic Position Sensor A Comparison of Two Image Registration Methods, Chest, 118(6):1783-1787.

Song et al., 2012, Autonomous and stable tracking of endoscope instrument tools with monocular camera, Advanced Intelligent Mechatronics (AIM), 2012 IEEE-ASME International Conference on. IEEE.

Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.

Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.

Wilson et al., 2008, a buyer's guide to electromagnetic tracking systems for clinical applications, Proc. of SPCI, 6918:69182B-1 p. 6918B-11.

Yip et al., 2012, Tissue tracking and registration for image-guided surgery, IEEE transactions on medical imaging 31(11):2169-2182.

Zhou et al., 2010, Synthesis of stereoscopic views from monocular endoscopic videos, Computer Vision and Pattern Recognition Workshops (CVPRW), 2010 IEEE Computer Society Conference on IEEE.

\* cited by examiner

INSTRUMENT IMAGE RELIABILITY SYSTEMS AND METHODS

CROSS-REFERENCE TO RELATED APPLICATION(S)

This application claims the benefit of U.S. Provisional Application No. 62/894,601, filed Aug. 30, 2019, which is hereby incorporated by reference in its entirety.

TECHNICAL FIELD

This disclosure relates generally to systems and methods for navigation of medical instruments, and more particularly to image-based analysis for navigating robotically-controlled medical instruments.

BACKGROUND

Medical procedures such as endoscopy (e.g., bronchoscopy) may involve accessing and visualizing the inside of a patient's lumen (e.g., airways) for diagnostic and/or therapeutic purposes. During a procedure, a flexible tubular tool or instrument, such as an endoscope, may be inserted into the patient's body. In some instances, a second instrument can be passed through the endoscope to a tissue site identified for diagnosis and/or treatment.

Bronchoscopy is a medical procedure that allows a physician to examine the inside conditions of airways in a patient's lungs, such as bronchi and bronchioles. During the medical procedure, a thin, flexible tubular tool or instrument, known as a bronchoscope, may be inserted into the patient's mouth and passed down the patient's throat into his or her lung airways towards a tissue site identified for subsequent diagnosis and/or treatment. The bronchoscope can have an interior lumen (a "working channel") providing a pathway to the tissue site, and catheters and various medical tools can be inserted through the working channel to the tissue site.

In certain medical procedures, surgical robotic systems may be used to control the insertion and/or manipulation of the surgical tools. Surgical robotic systems may include at least one robotic arm or other instrument positioning device including a manipulator assembly used to control the positioning of the surgical tool during the procedures.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
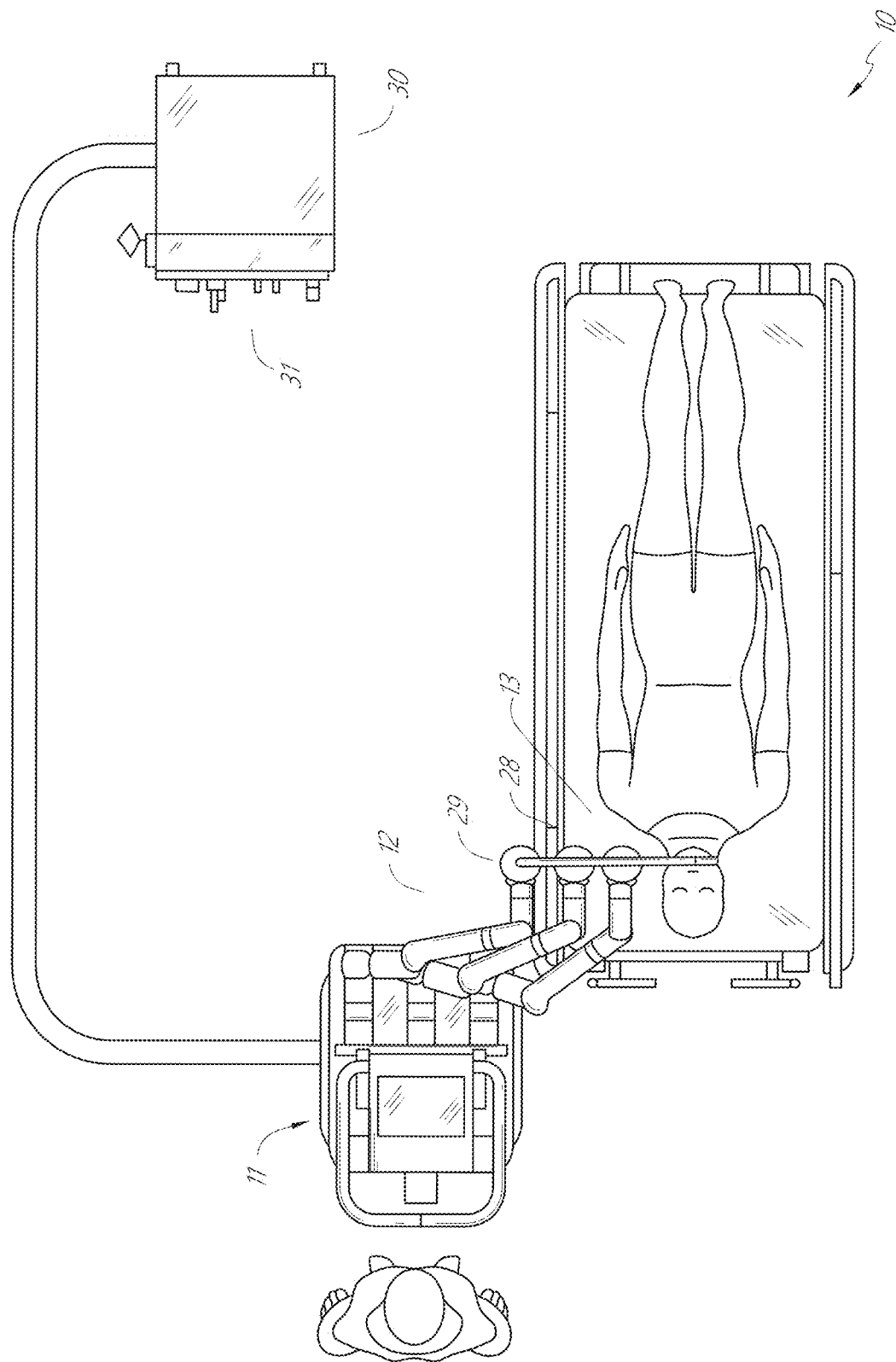
FIG. 1 illustrates an embodiment of a cart-based robotic system arranged for diagnostic and/or therapeutic bronchoscopy procedure(s).
Figure 2:
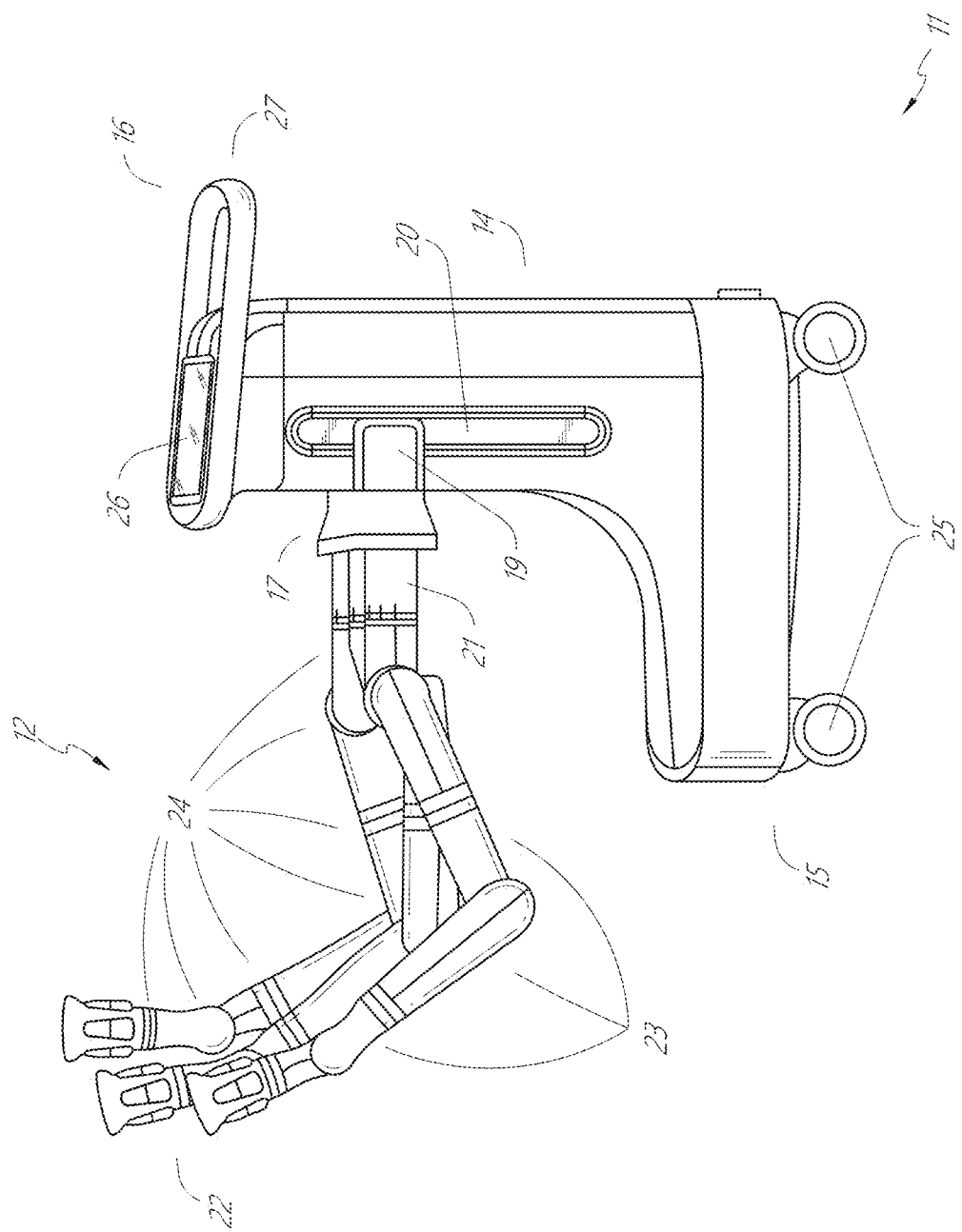
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and the endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
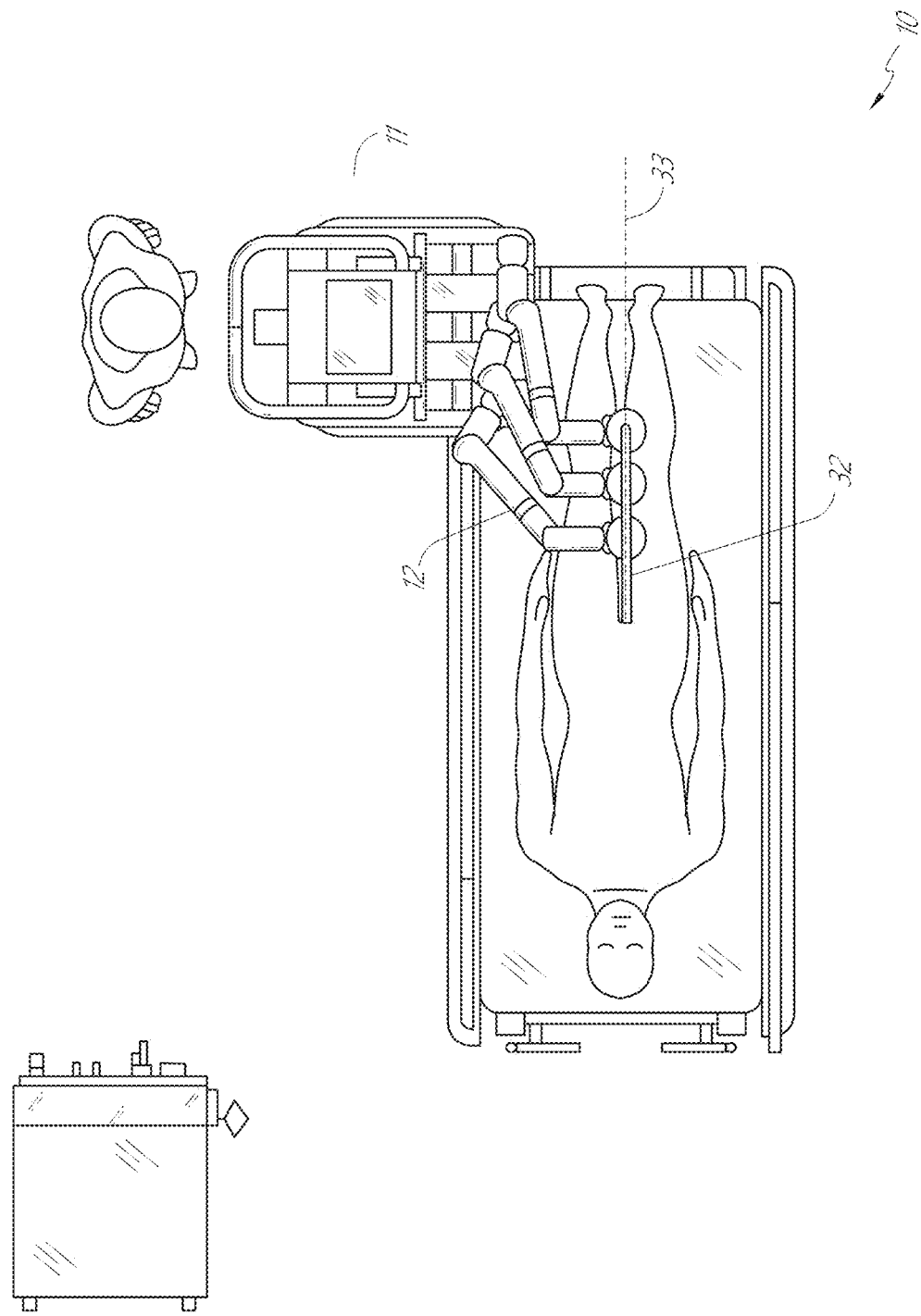
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopy procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
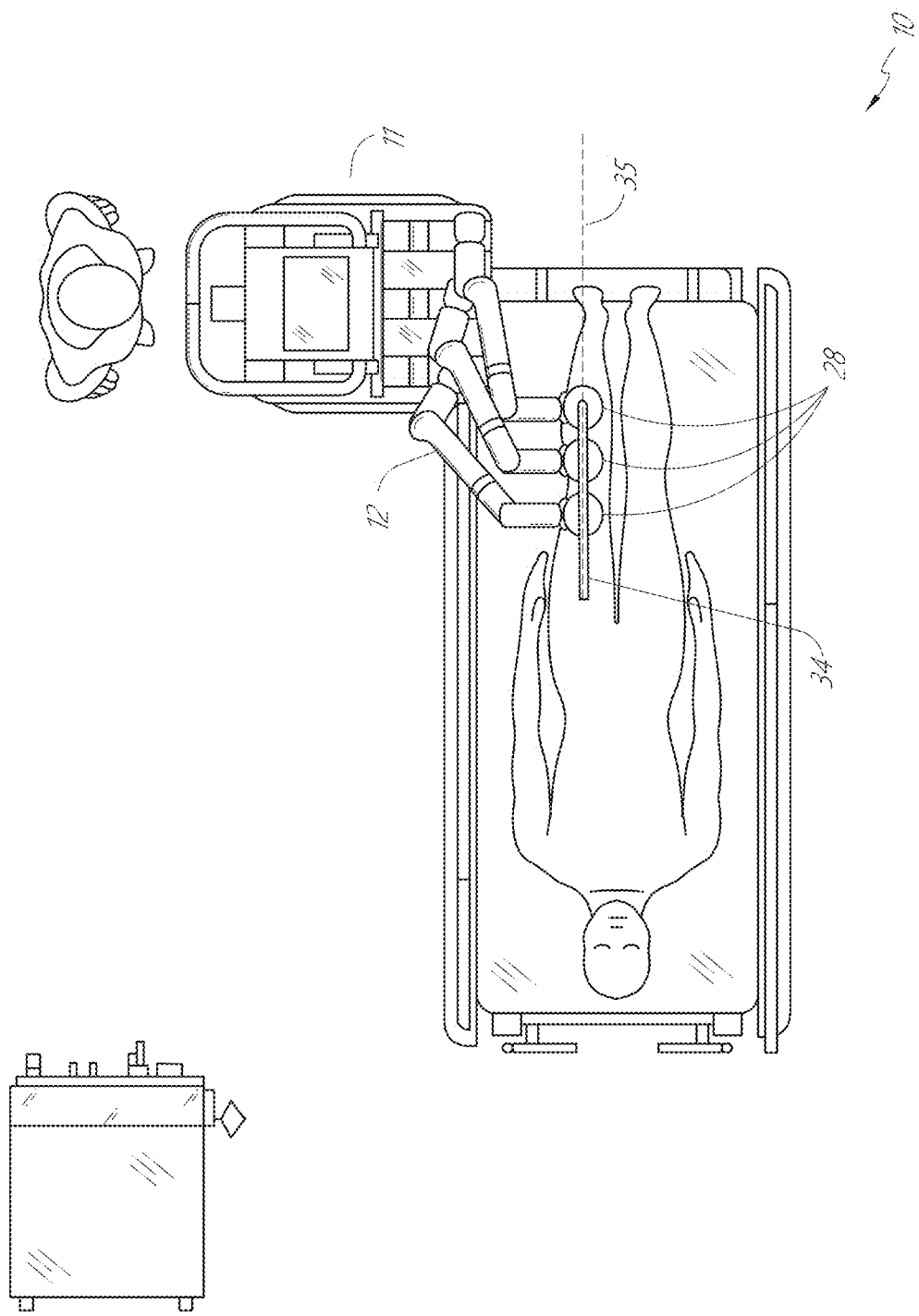
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopy procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart 11 may be positioned around the patient's upper abdomen in order to reach alternative vascular access points, such as, for example, the carotid and brachial arteries near the shoulder and wrist.

B. Robotic System—Table.

Figure 5:
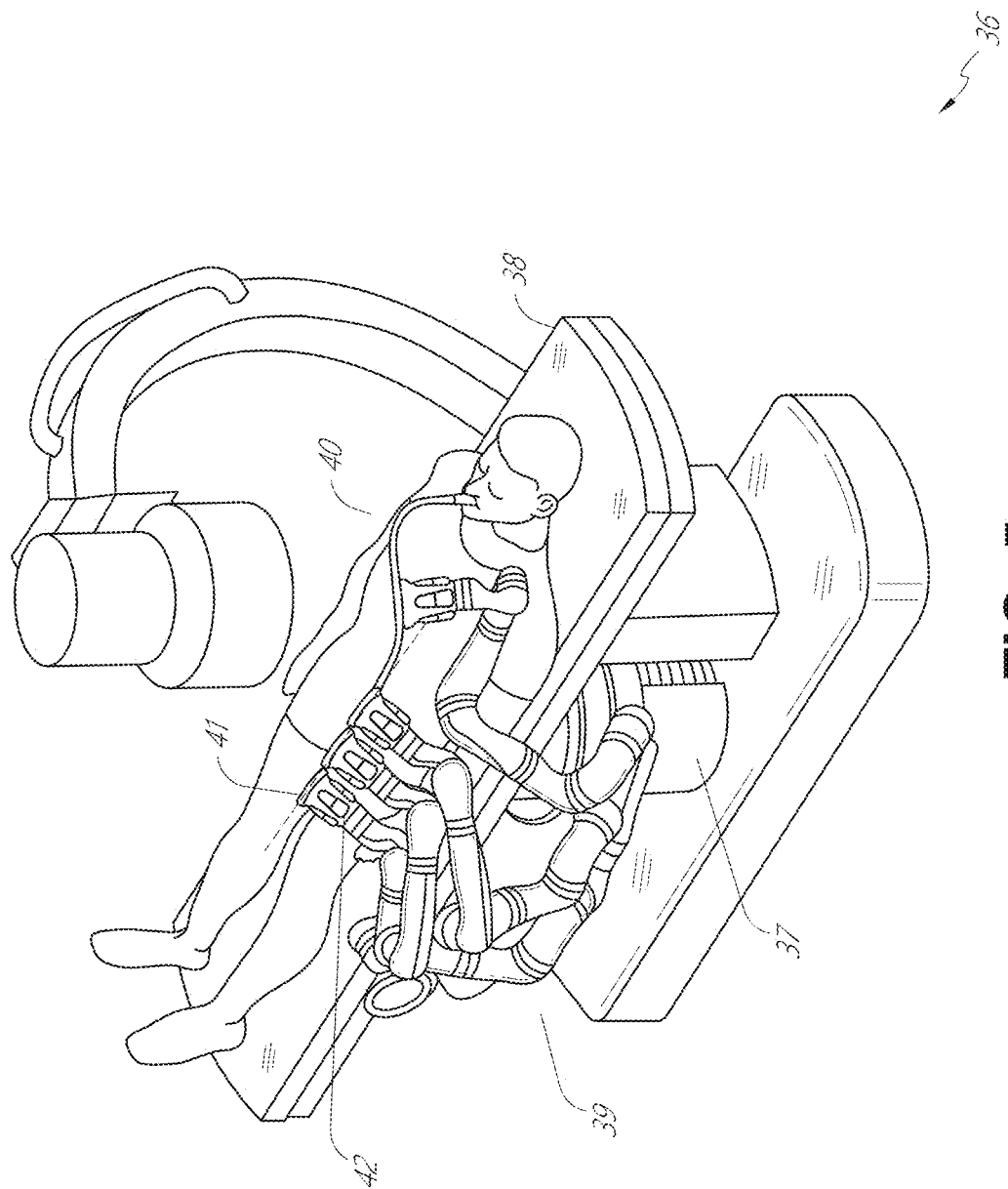
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
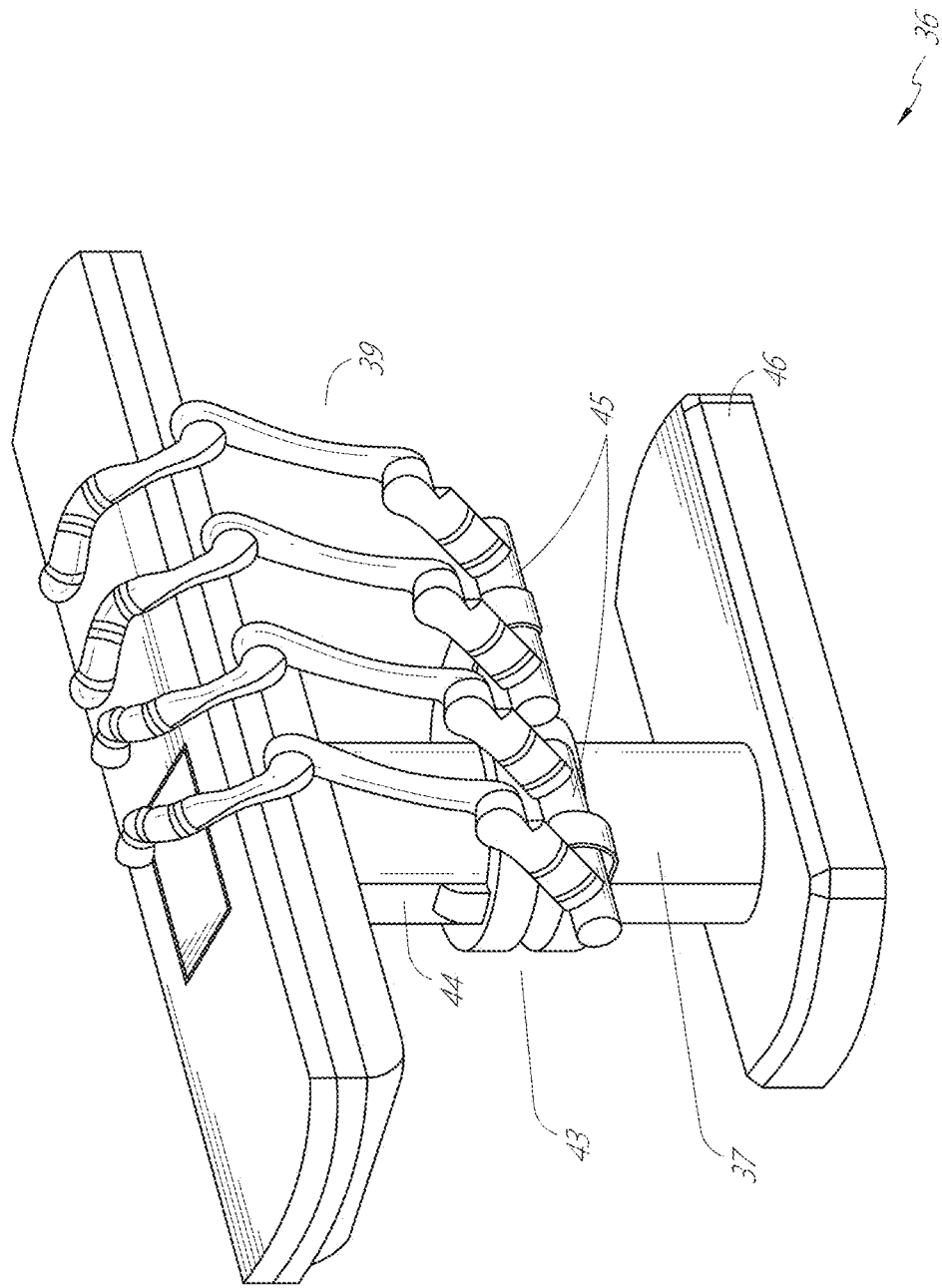
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
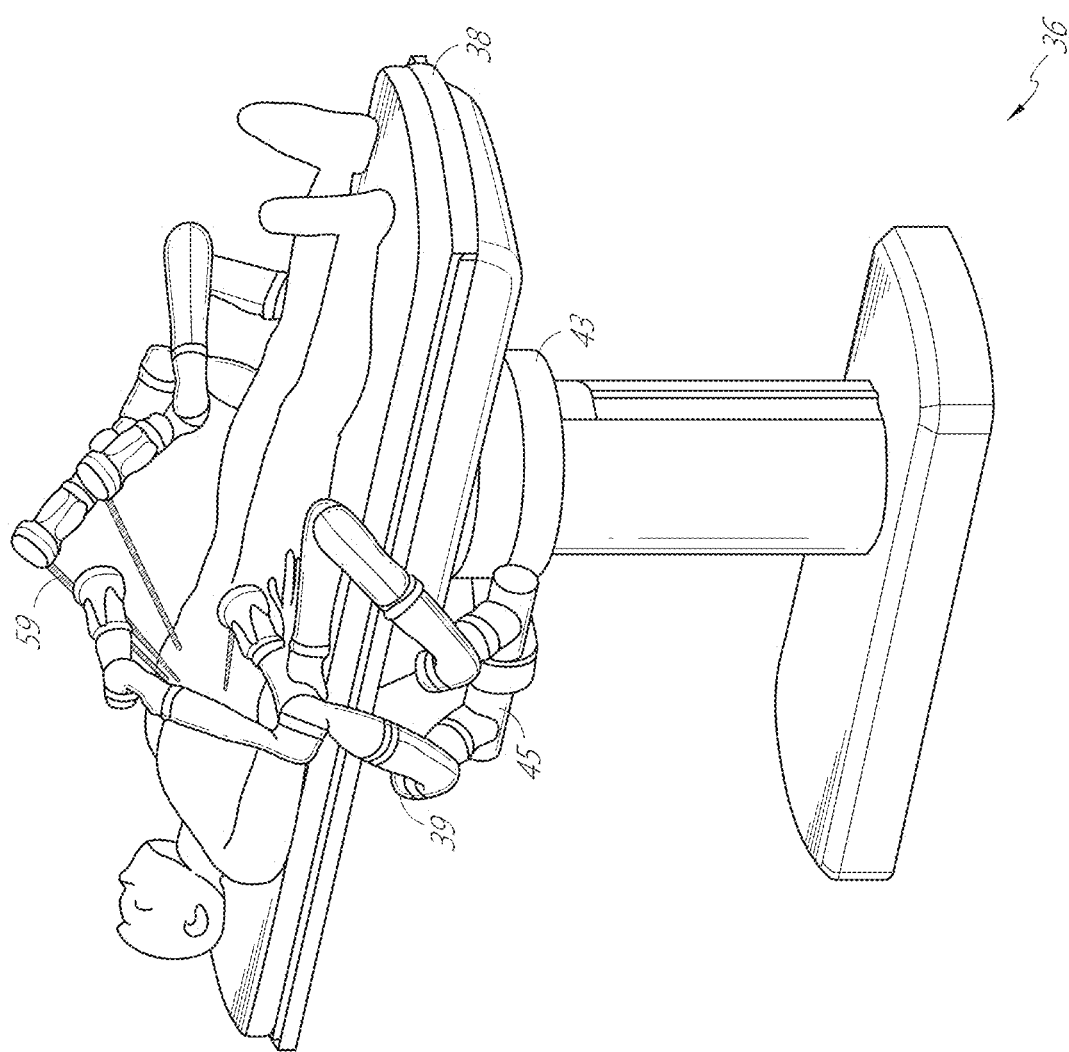
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages 43, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
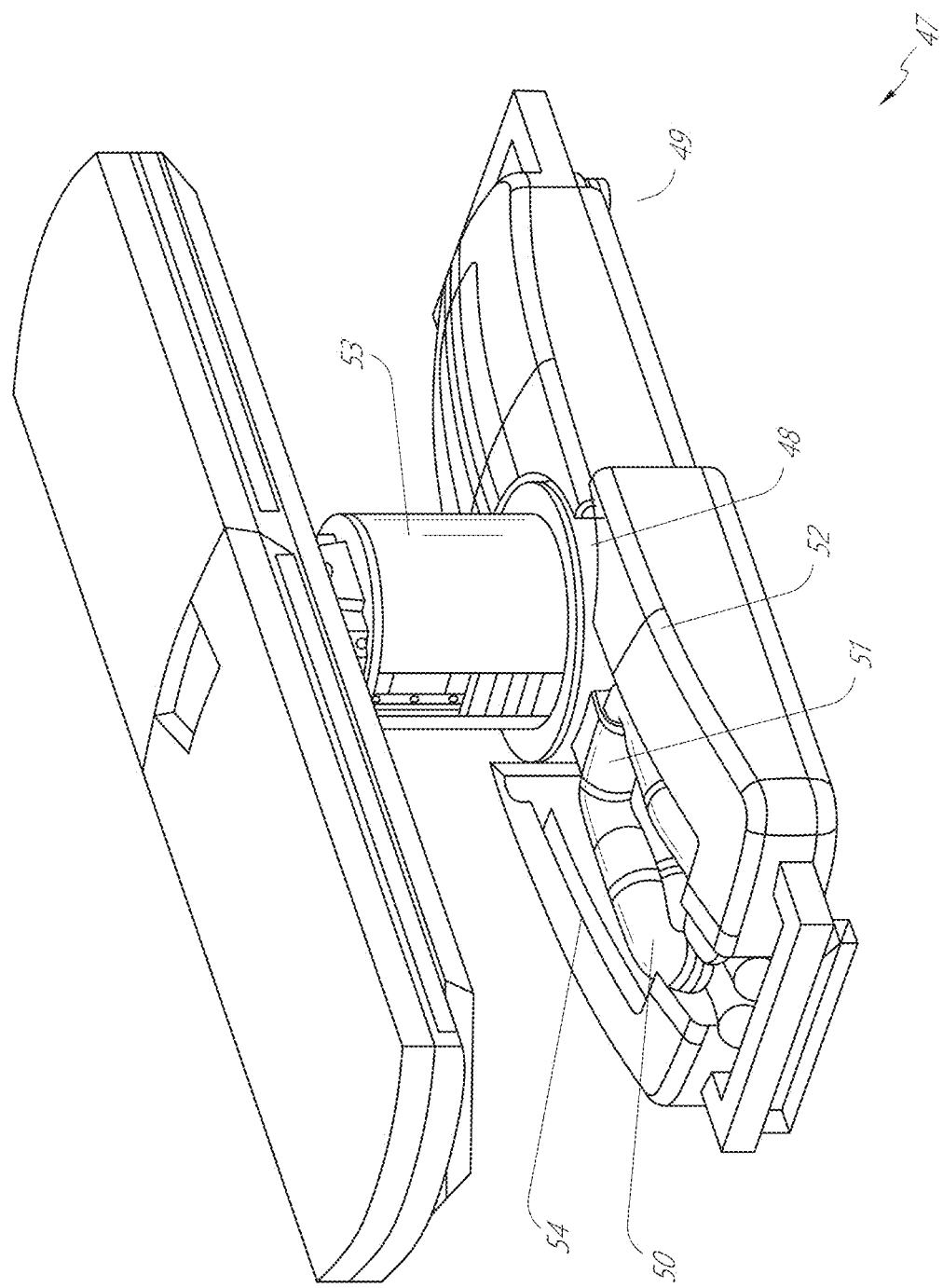
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
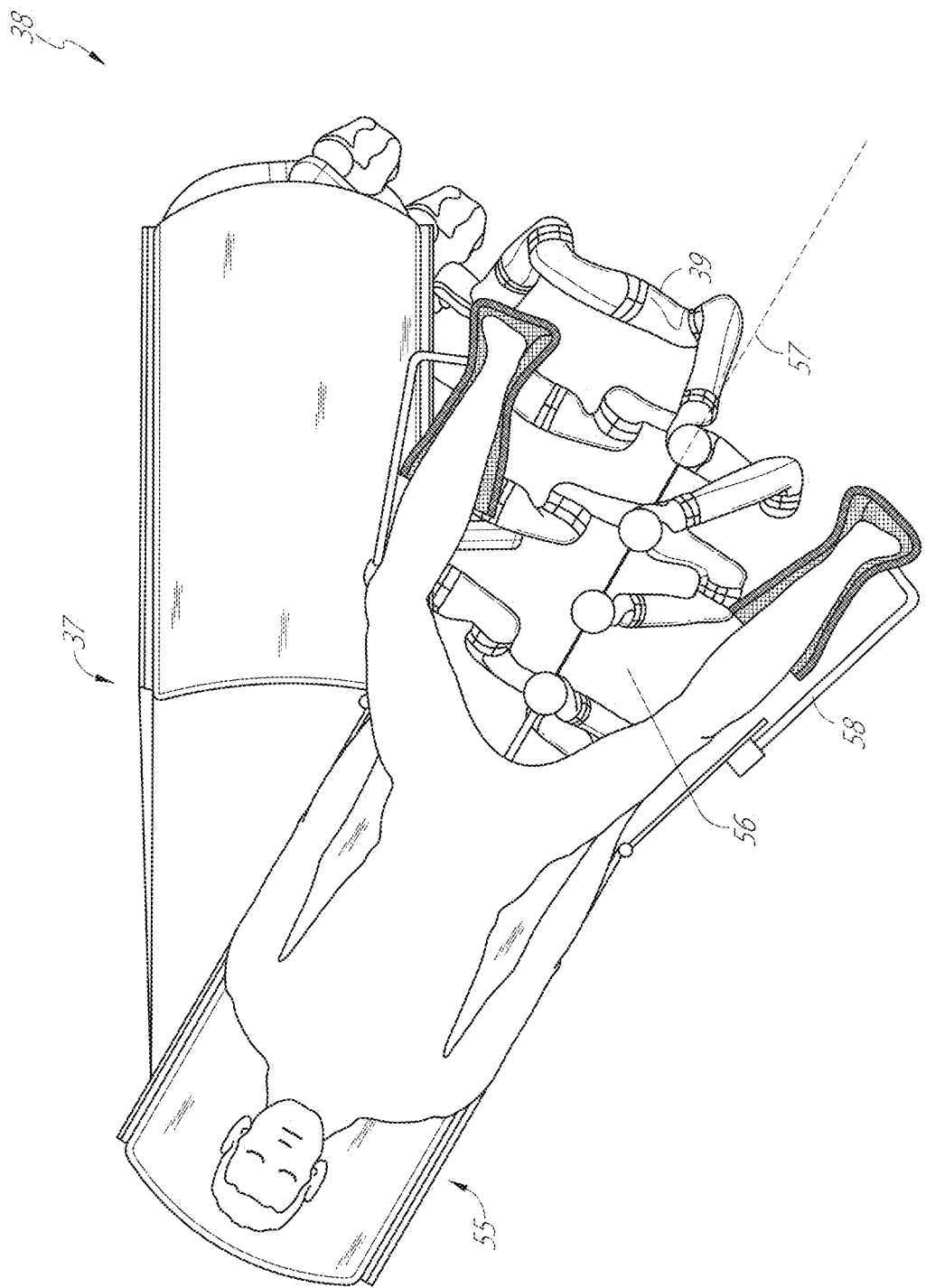
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopy procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopy procedure. As shown, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
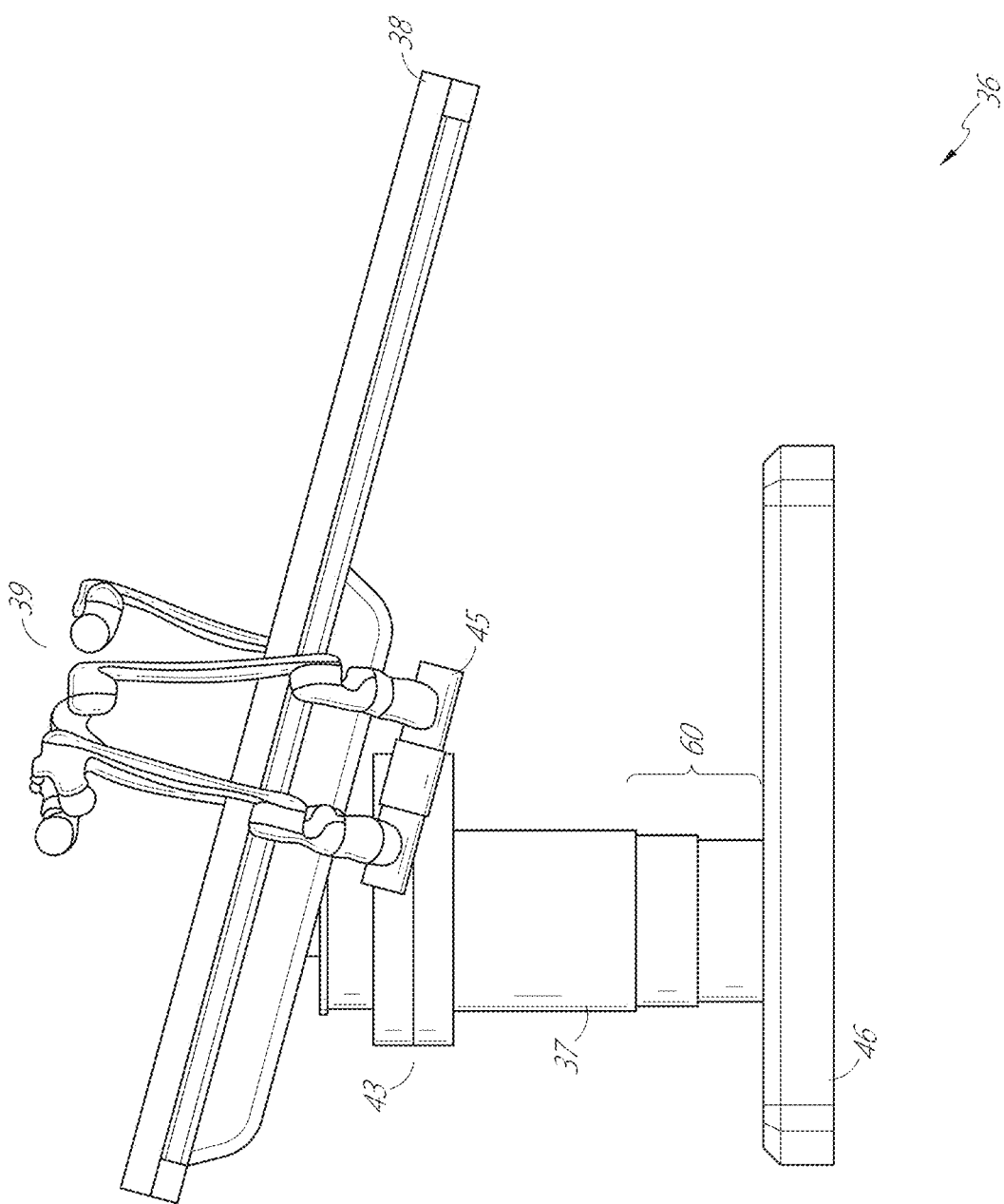
FIG. 10 illustrates an embodiment of the table-based robotic system of FIGS. 5-9 with pitch or tilt adjustment.

To accommodate laparoscopy procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
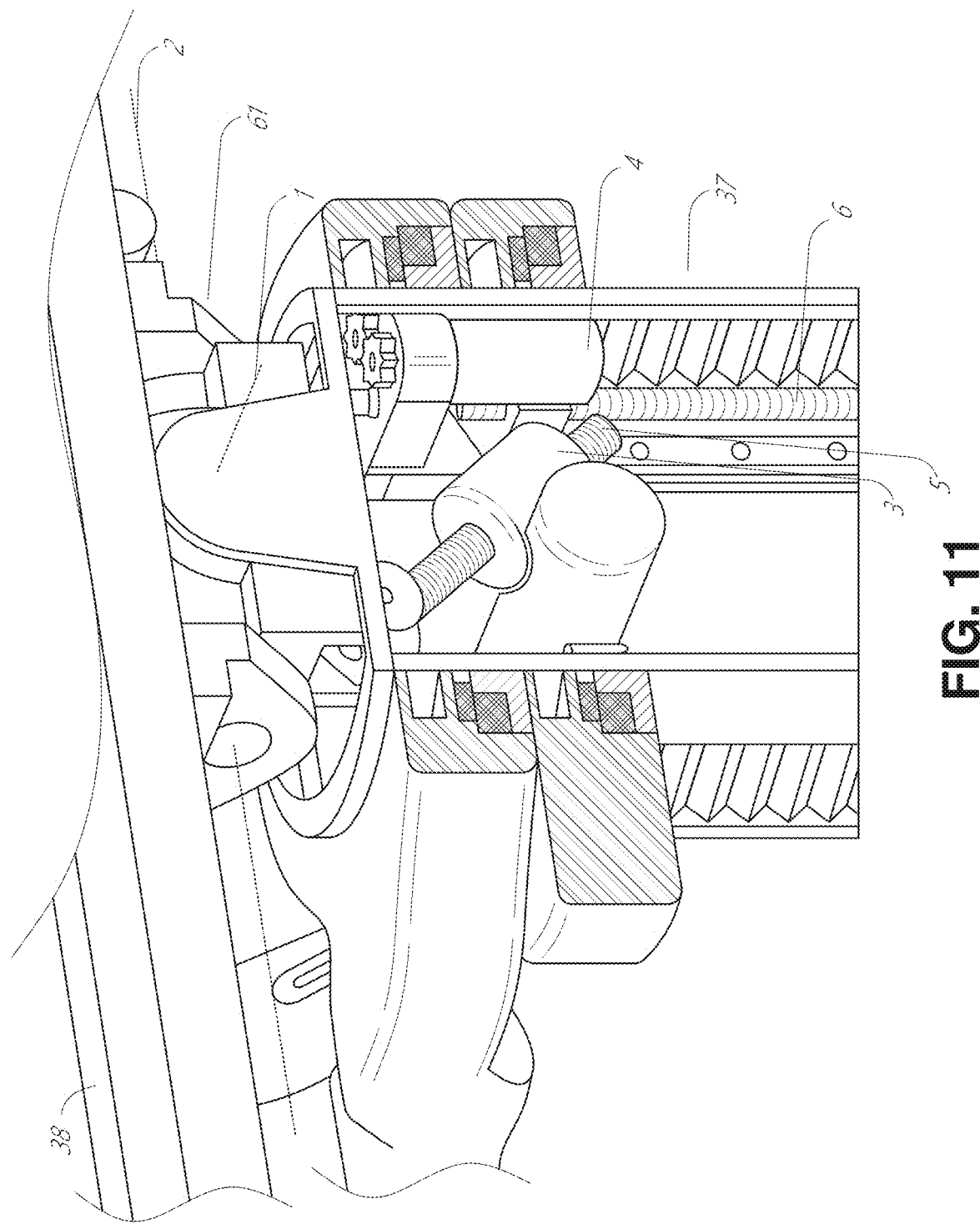
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
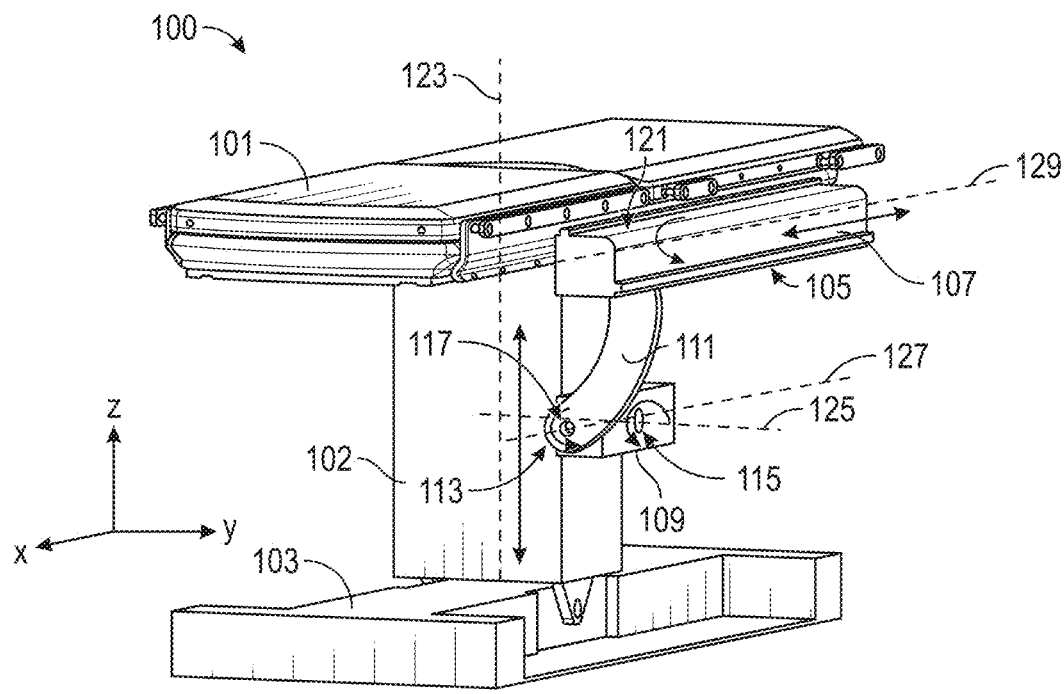
FIG. 12 illustrates an alternative embodiment of a table-based robotic system.
Figure 13:
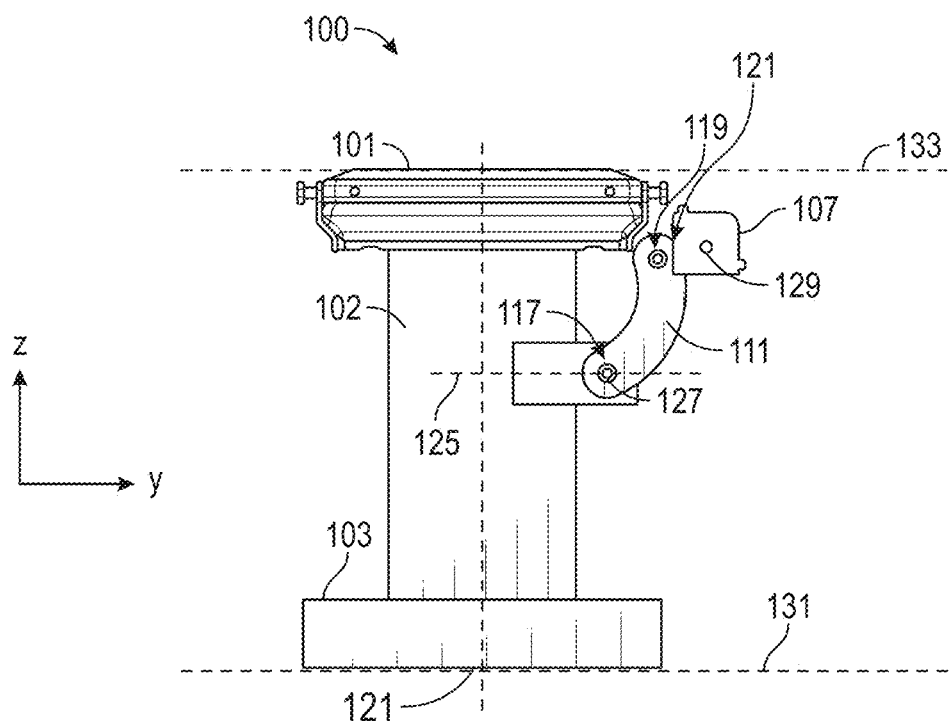
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
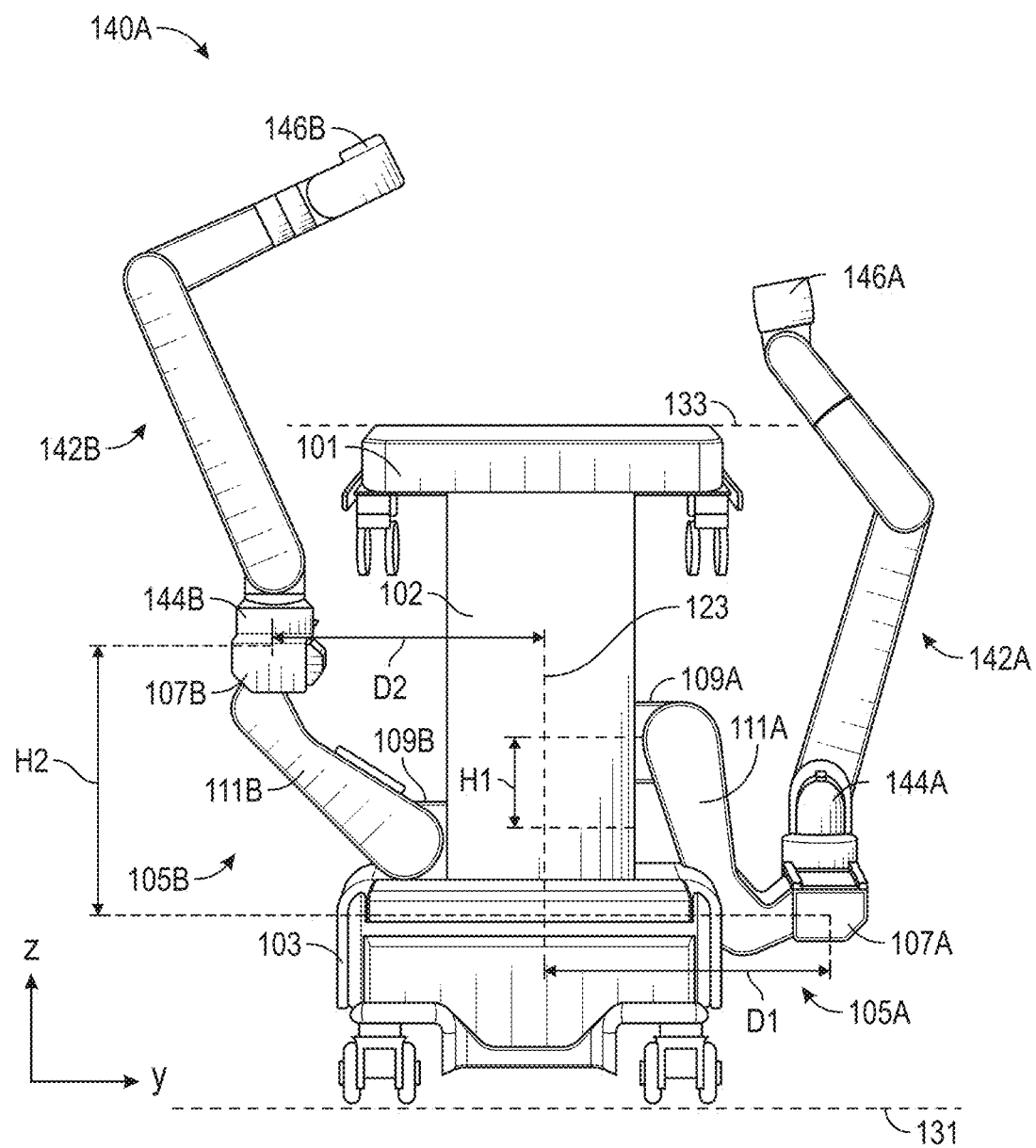
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
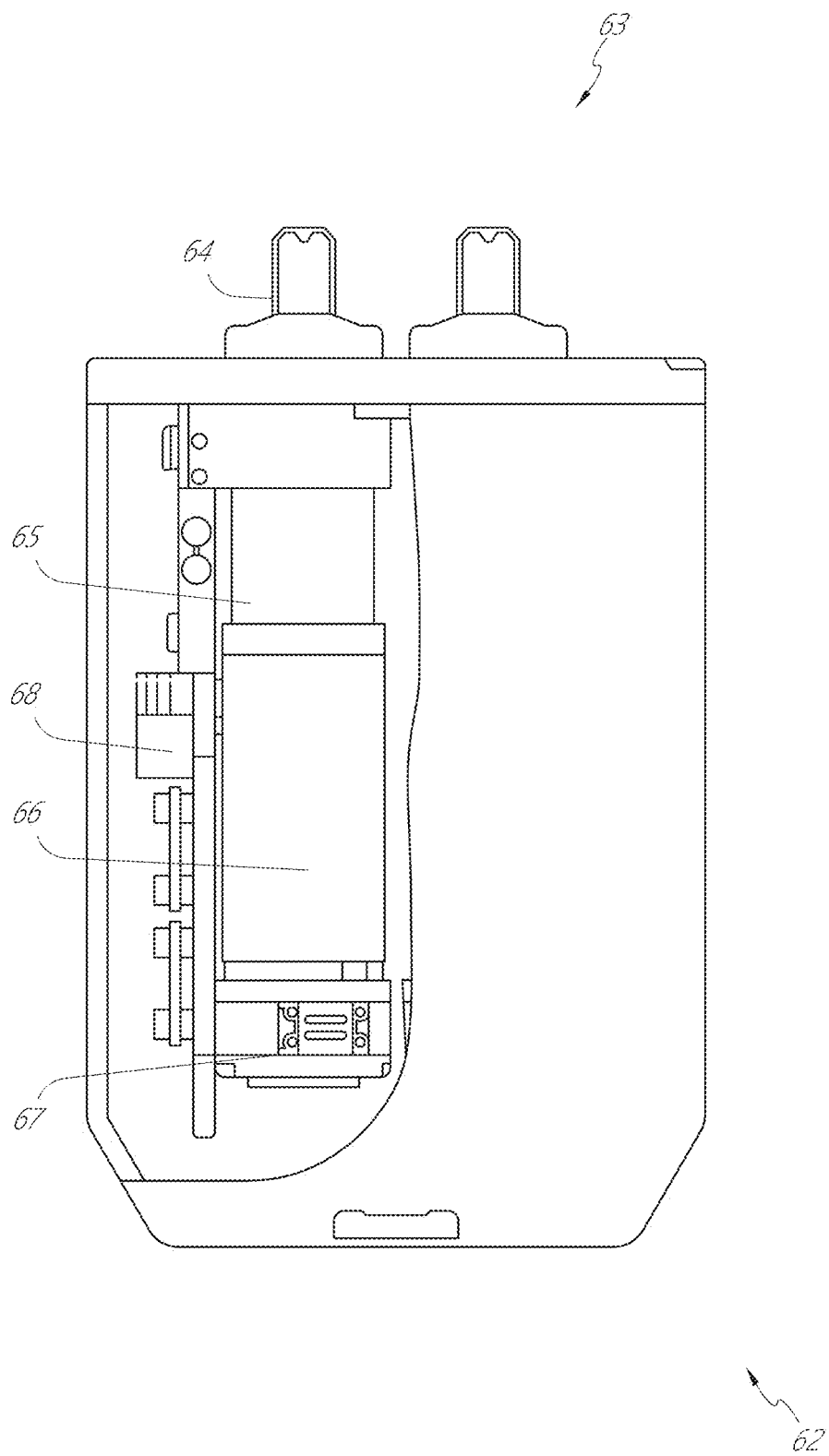
FIG. 15 illustrates an exemplary instrument driver.
Figure 16:
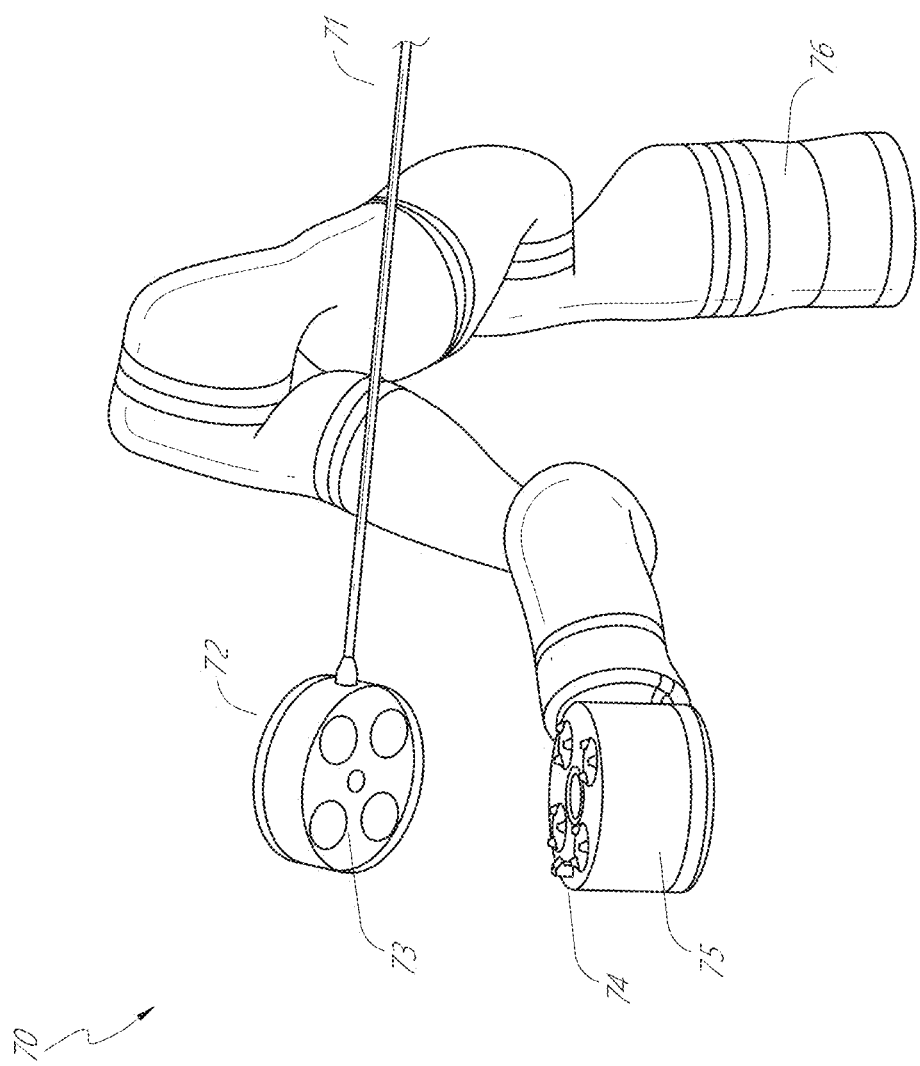
FIG. 16 illustrates an exemplary medical instrument with a paired instrument driver.
Figure 17:
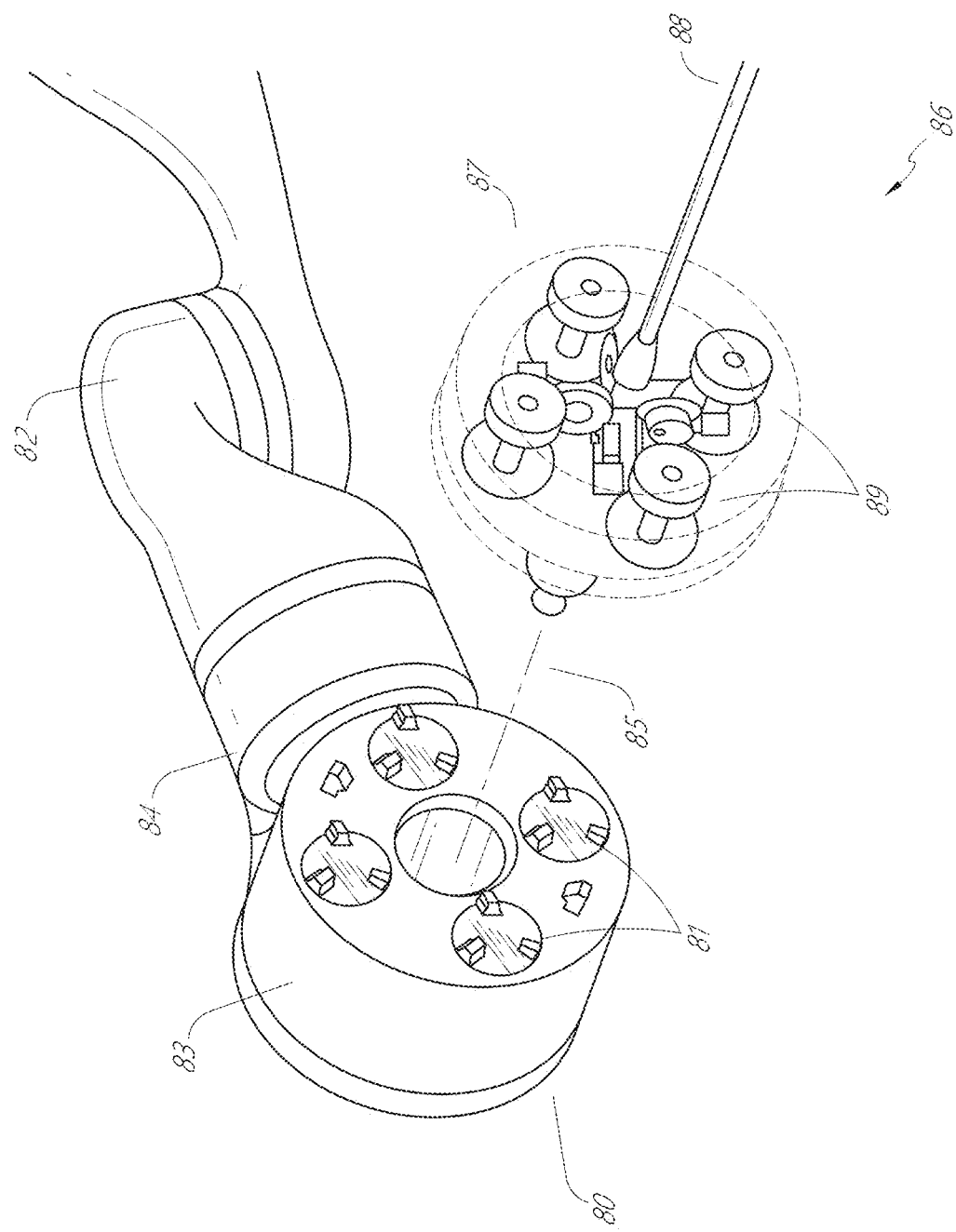
FIG. 17 illustrates an alternative design for an instrument driver and instrument where the axes of the drive units are parallel to the axis of the elongated shaft of the instrument.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 may be independently controlled and motorized, and the instrument driver 62 may provide multiple (e.g., four as shown in FIGS. 16 and 17) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys, or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on the force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on the torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71 or in the wrist at the distal portion of the elongated shaft 71. During a surgical procedure, such as a laparoscopic, endoscopic or hybrid procedure, these tendons may be coupled to a distally mounted end effector, such as a wrist, grasper, or scissor. Under such an arrangement, torque exerted on the drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at the distal end of the elongated shaft 71, where the tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from the tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but also exhibits more limited bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopy procedure.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
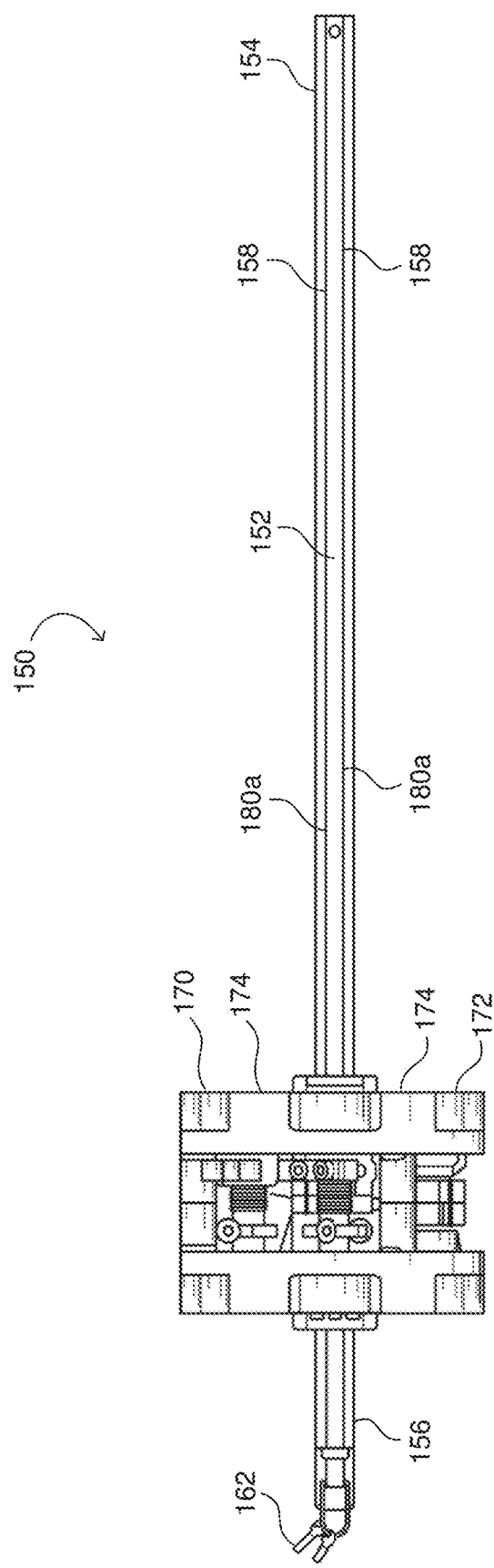
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
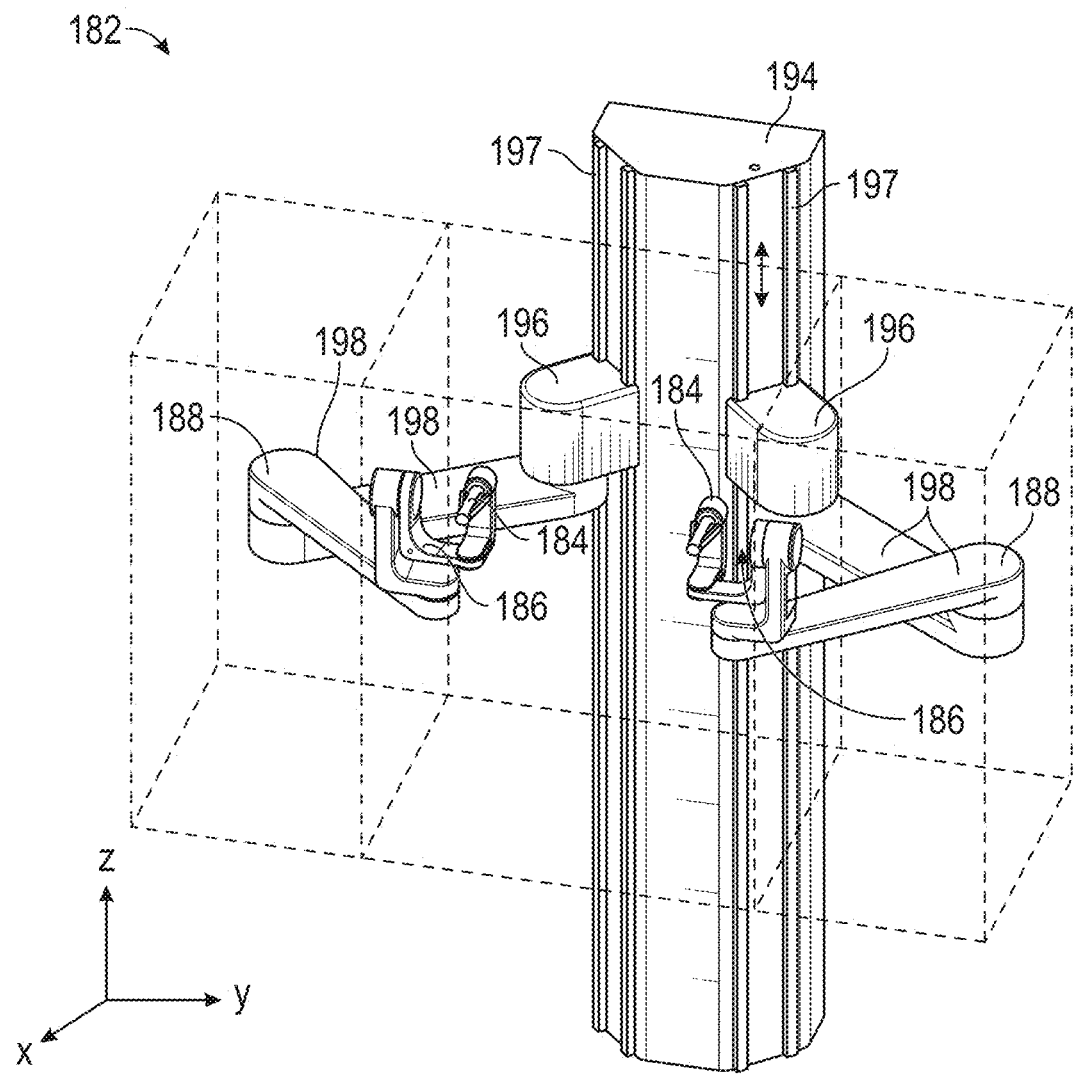
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
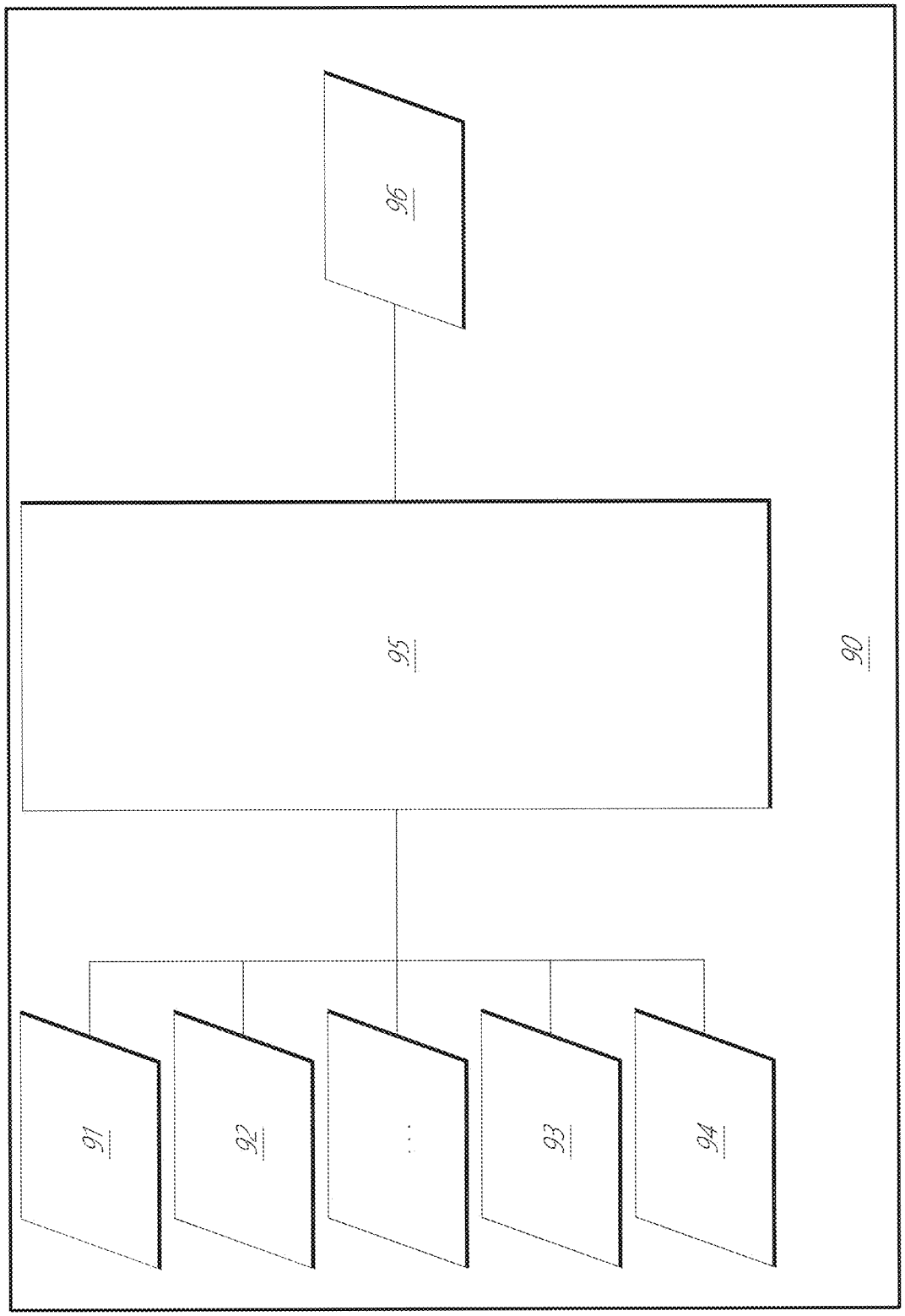
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces, and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). In some embodiments, the preoperative model data 91 may include data from, e.g., fluoroscopy, magnetic resonance imaging (MRI), ultrasound imaging, and/or x-rays. The use of center-line geometry is discussed in U.S. patent application Ser. No. 14/523,760, the contents of which are herein incorporated in its entirety. Network topological models may also be derived from the CT images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed, and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Navigation of Luminal Networks.

The various robotic systems discussed above can be employed to perform a variety of medical procedures, such as endoscopic and laparoscopy procedures. During certain procedures, a medical instrument, such as a robotically-controlled medical instrument, is inserted into a patient's body. Within the patient's body, the instrument may be positioned within a luminal network of the patient. As used herein, the term "luminal network" refers to any cavity structure within the body, whether comprising a plurality of lumens or branches (e.g., a plurality of branched lumens, as in the lung or blood vessels) or a single lumen or branch (e.g., within the gastrointestinal tract). During the procedure, the instrument may be moved (e.g., navigated, guided, driven, etc.) through the luminal network to one or more areas of interest. Movement of the instrument through the system may be aided by the navigation or localization system 90 discussed above, which can provide positional information about the instrument to a physician controlling the robotic system.

Figure 21:
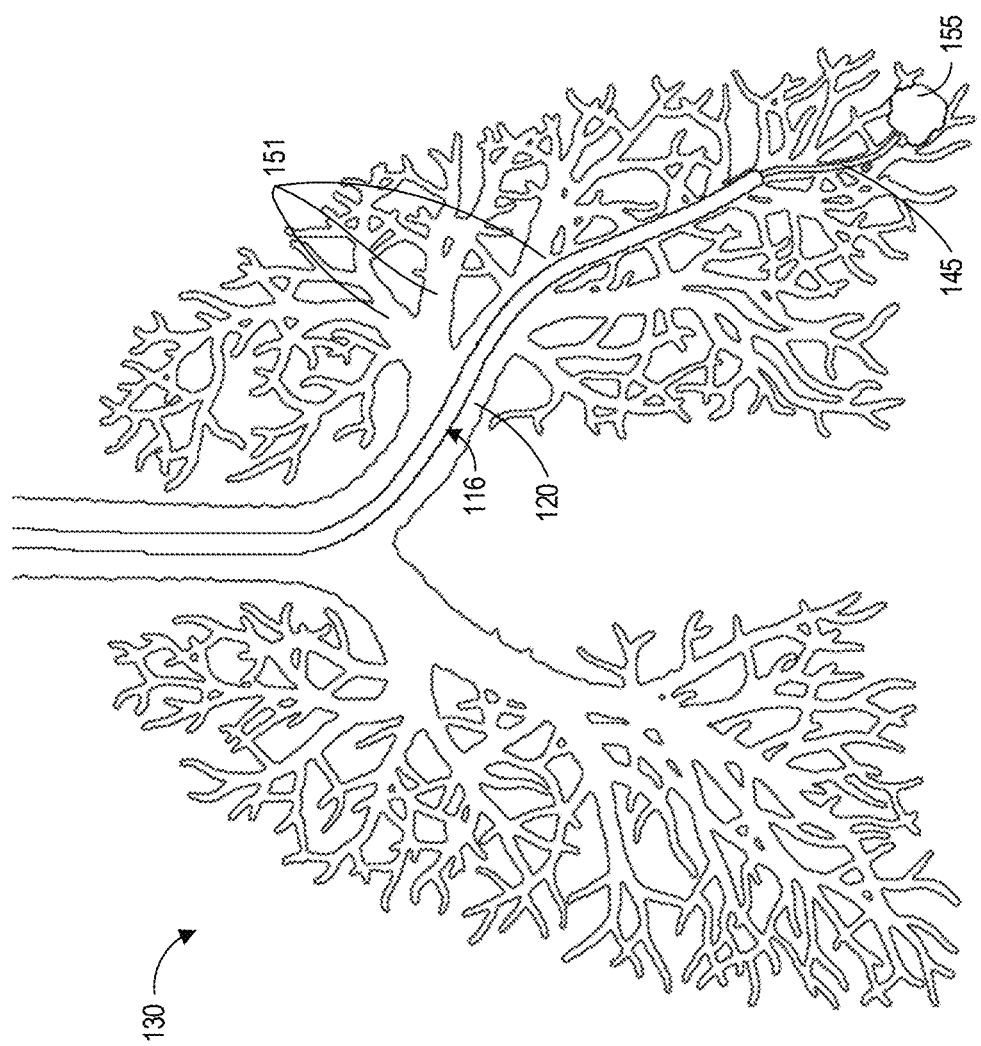
FIG. 21 illustrates an example luminal network of a patient.

FIG. 21 illustrates an example luminal network 130 of a patient. In the illustrated embodiment, the luminal network 130 is a bronchial network of pathways 151 (i.e., lumens, branches) of the patient's lung. Although the illustrated luminal network 130 is a bronchial network of airways within the patient's lung, this disclosure is not limited to only the illustrated example. The robotic systems and methods described herein may be used to navigate any type of luminal network, such as bronchial networks, renal networks, cardiovascular networks (e.g., arteries and veins), gastrointestinal tracts, urinary tracts, etc.

As illustrated, the luminal network 130 comprises a plurality of pathways 151 that are arranged in a branched structure. In general, the luminal network 130 comprises a three-dimensional structure. For ease of illustration, FIG. 21 represents the luminal network 130 as a two-dimensional structure. This should not be construed to limit the present disclosure to two-dimensional luminal networks in any way.

FIG. 21 also illustrates an example of a medical instrument positioned within the luminal network 130. The medical instrument is navigated through the luminal network 130 towards an area of interest (e.g., nodule 155) for diagnosis and/or treatment. In the illustrated example, the nodule 155 is located at the periphery of the pathways 151, although the area(s) of interest can be positioned anywhere within the luminal network 130 depending on the patient and procedure.

In the illustrated example, the medical instrument comprises an endoscope 116. The endoscope 116 can include a sheath 120 and a leader 145. In some embodiments, the sheath 120 and the leader 145 may be arranged in a telescopic manner. For example, the leader 145 may be slidably positioned inside a working channel of the sheath 120. The sheath 120 may have a first diameter, and its distal end may not be able to be positioned through the smaller-diameter pathways 151 around the nodule 155. Accordingly, the leader 145 may be configured to extend from the working channel of the sheath 120 the remaining distance to the nodule 155. The leader 145 may have a lumen through which instruments, for example biopsy needles, cytology brushes, and/or tissue sampling forceps, can be passed to the target tissue site of the nodule 155. In such implementations, both the distal end of the sheath 120 and the distal end of the leader 145 can be provided with EM instrument sensors (e.g., EM instrument sensors 305 in FIG. 23) for tracking their position within the pathways 151. This telescopic arrangement of the sheath 120 and the leader 145 may allow for a thinner design of the endoscope 116 and may improve a bend radius of the endoscope 116 while providing a structural support via the sheath 120.

In other embodiments, the overall diameter of the endoscope 116 may be small enough to reach the periphery without the telescopic arrangement, or may be small enough to get close to the periphery (e.g., within about 2.5-3 cm) to deploy medical instruments through a non-steerable catheter. The medical instruments deployed through the endoscope 116 may be equipped with EM instrument sensors (e.g., EM instrument sensors 305 in FIG. 23), and the image-based pathway analysis and mapping techniques described below can be applied to such medical instruments.

As shown, to reach the nodule 155, the instrument (e.g., endoscope 116) must be navigated or guided through the pathways 151 of the luminal network. An operator (such as a physician) can control the robotic system to navigate the instrument to the nodule 155. The operator may provide inputs for controlling the robotic system.

Figure 22:
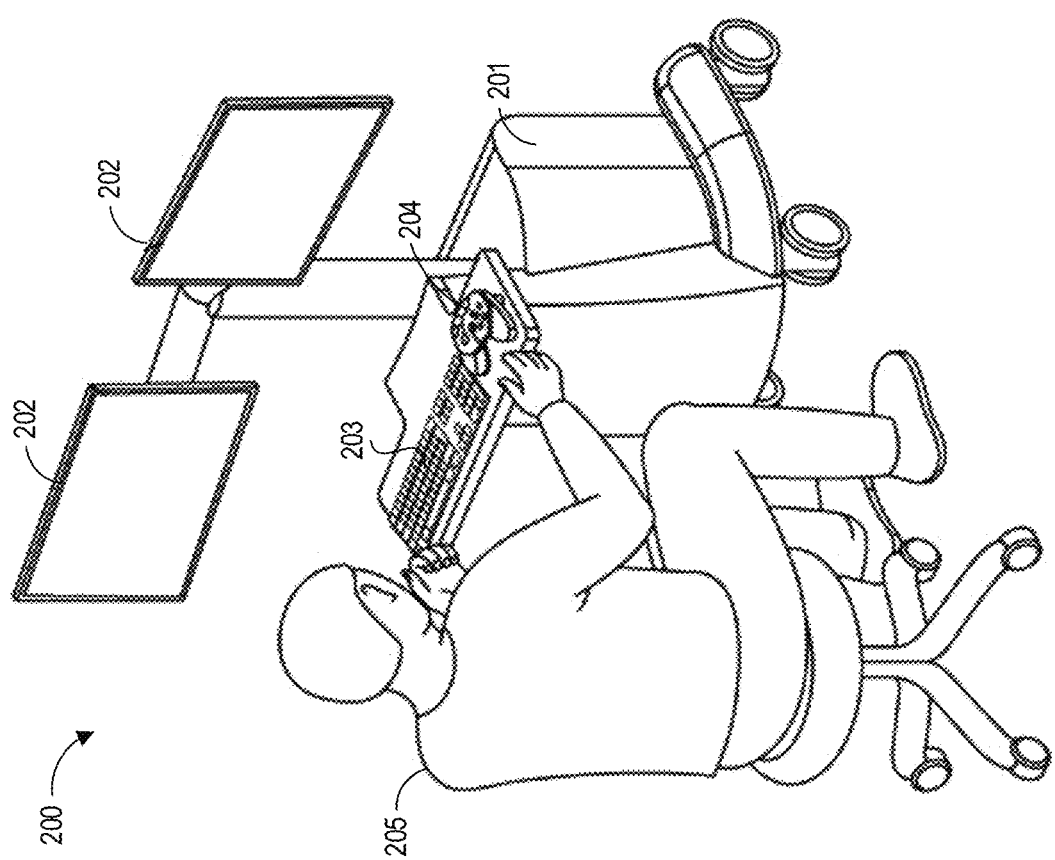
FIG. 22 illustrates an example command console that can be used with some implementations of the robotic systems described herein.

FIG. 22 illustrates an example command console 200 that can be used with some implementations of the robotic systems described herein. The operator may provide the inputs for controlling the robotic system, for example, to navigate or guide the instrument to an area of interest such as nodule 155, via the command console 200. The command console 200 may be embodied in a wide variety of arrangements or configurations. In the illustrated example, the command console 200 includes a console base 201, displays 202 (e.g., monitors), and one or more control modules (e.g., keyboard 203 and joystick 204). A user 205 (e.g., physician or other operator) can remotely control the medical robotic system (e.g., the systems described with reference to FIGS. 1-20) from an ergonomic position using the command console 200.

The displays 202 may include electronic monitors (e.g., LCD displays, LED displays, touch-sensitive displays), virtual reality viewing devices (e.g., goggles or glasses), and/or other display devices. In some embodiments, one or more of the displays 202 displays position information about the instrument, for example, as determined by the localization system 90 (FIG. 20). In some embodiments, one or more of the displays 202 displays a preoperative model of the patient's luminal network 130. The positional information can be overlaid on the preoperative model. The displays 202 can also display image information received from a camera or another sensing device positioned on the instrument within the luminal network 130. In some embodiments, a model or representation of the instrument is displayed with the preoperative model to help indicate a status of a surgical or medical procedure.

In some embodiments, the console base 201 includes a central processing unit (e.g., CPU or processor), a memory unit (e.g., computer-readable memory), a data bus, and associated data communication ports that are responsible for interpreting and processing signals such as camera imagery and tracking sensor data, e.g., from a medical instrument positioned within a luminal network of a patient.

The console base 201 may also process commands and instructions provided by the user 205 through control modules 203, 204. In addition to the keyboard 203 and joystick 204 shown in FIG. 22, the control modules may include other devices, such as computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.). Using the control modules 203, 204 of the command console 200, the user 205 may navigate an instrument through the luminal network 130.

Figure 23:
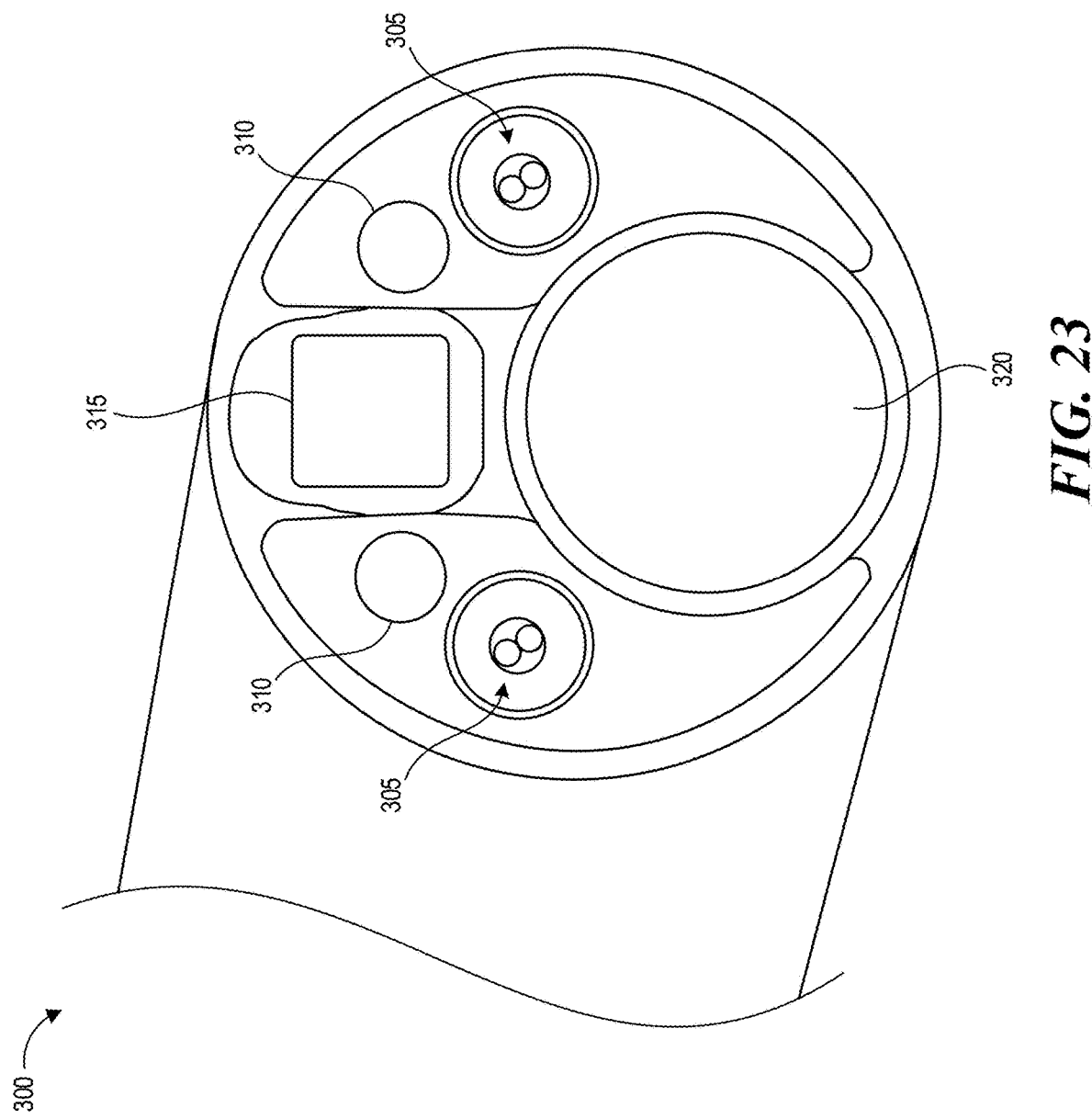
FIG. 23 illustrates a detail view of a distal end of an example medical instrument.

FIG. 23 illustrates a detailed view of a distal end of an example medical instrument 300. The medical instrument 300 may be representative of the endoscope 116 or leader 145 of FIG. 21. The medical instrument 300 may be representative of any medical instrument described throughout the disclosure, such as the endoscope 13 of FIG. 1, the ureteroscope 32 of FIG. 3, the laparoscope 59 of FIG. 9, etc. In FIG. 23, the distal end of the instrument 300 includes an imaging device 315, illumination sources 310, and ends of EM sensor coils 305, which form an EM instrument sensor. The distal end further includes an opening to a working channel 320 of the instrument 300 through which surgical instruments, such as biopsy needles, cytology brushes, forceps, etc., may be inserted along the instrument shaft, allowing access to the area near the instrument tip.

EM coils 305 located on the distal end of the instrument 300 may be used with an EM tracking system to detect the position and orientation of the distal end of the instrument 300 while it is positioned within a luminal network. In some embodiments, the coils 305 may be angled to provide sensitivity to EM fields along different axes, giving the disclosed navigational systems the ability to measure a full 6 degrees of freedom (DoF): three positional DoF and three angular DoF. In other embodiments, only a single coil 305 may be disposed on or within the distal end with its axis oriented along the instrument shaft. Due to the rotational symmetry of such a system, it may be insensitive to roll about its axis, so only five degrees of freedom may be detected in such an implementation. Alternatively or additionally, other types of position sensors may be employed.

The illumination sources 310 provide light to illuminate a portion of an anatomical space. The illumination sources 310 can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, the illumination sources 310 can include light-emitting diodes (LEDs) located at the distal end of the instrument 300. In some embodiments, the illumination sources 310 can include one or more fiber optic fibers extending through the length of the endoscope to transmit light through the distal end from a remote light source, for example, an x-ray generator. Where the distal end includes multiple illumination sources 310, these can each be configured to emit the same or different wavelengths of light as one another.

The imaging device 315 can include any photosensitive substrate or structure configured to convert energy representing received light into electric signals, for example, a charge-coupled device (CCD) or complementary metal-oxide semiconductor (CMOS) image sensor. Some examples of the imaging device 315 can include one or more optical fibers, for example, a fiber optic bundle, configured to transmit light representing an image from the distal end 300 of the endoscope to an eyepiece and/or image sensor near the proximal end of the endoscope. The imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as command console 200. As mentioned above and as will be described in greater detail below, the images captured by the imaging device 315 (e.g., vision data 92 of FIG. 20) can be utilized by the navigation or localization system 95 to determine or estimate the position of the instrument (e.g., the position of the distal tip of the instrument 300) within a luminal network.

III. Image Management.

Embodiments of the disclosure relate to systems and techniques for management of images obtained during pathway (e.g., airway) analysis and/or mapping. Image management may refer to identifying, analyzing, filtering, utilizing, and/or modifying images obtained from an endoscope as described herein. For example, an image management system may capture an image of an interior of a luminal network using an imaging device positioned on an instrument within the luminal network, and the image management system may analyze the image to identify one or more airways shown in the image. The image management system may use preoperative model data (e.g., trained model from machine learning algorithms) to support the management of the images. For example, an image management system may be configured to identify images of a given luminal network that correspond to sufficiently reliable, clear, and/or otherwise quality images. In certain implementations, these systems and techniques may be used in conjunction with various other navigation and localization modalities (e.g., as described above with reference to FIG. 20).

A. Image Analysis.

During a medical procedure, images may be transferred from an imaging device of a medical instrument (e.g., an endoscope) to a display and/or a memory device. Endoscopic image devices provide direct vision perception to clinicians during navigation. Additionally or alternatively, the images may be analyzed by processing algorithms to determine a location of the medical device within the luminal network (e.g., using the localization module 95). However, the images captured during endoscopy can be difficult to interpret, particularly those images that are uninformative. In endoscopy, the uninformative images can include images that present a high degree of fluid artifacts, specular reflection, and/or blurness (or blurriness) that may be due, for example, to fast camera motion. A computerized algorithm for automatically identifying these uninformative images would benefit clinicians. For example, such images may be discarded and/or labeled as uninformative, unreliable, and/or low quality. Clinicians may also benefit from subsequent image processing algorithms described herein. An image management system advantageously allows a user (e.g., surgeon, medical practitioner, etc.) to avoid unhelpful images that may be obtained from the imaging device. Additionally or alternatively, the system can allow a computerized algorithm better determine a location of the medical instrument within the luminal network.

The ability to navigate inside a luminal network may be a feature of the robotically-controlled surgical systems described herein, and may involve localization. As used herein, localization may refer to locating or determining the position of an instrument within the luminal network. The determined position may be used to help guide the instrument to one or more particular areas of interest within the luminal network. In some embodiments, the robotically-controlled surgical systems utilize one or more independent sensing modalities to provide intraoperative navigation for the instrument. As shown in FIG. 20, the independent sensing modalities may provide position data (e.g., EM data 93), vision data 92, and/or robotic command and kinematics data 94. These independent sensing modalities may include estimation modules configured to provide independent estimates of position. The independent estimates can then be combined into one navigation output, for example, using localization module 95, which can be used by the system or displayed to the user. Image-based airway analysis and mapping may provide an independent sensing modality, based on vision data 92, that can provide an independent estimate of position. In particular, in some instances image-based airway analysis and mapping provides a combination of a sensing modality and a state/position estimation module that estimates which lumen or branch of a luminal network an imaging device of the instrument is located based on one or more images captured by the imaging device. In some embodiments, the estimate provided by image-based airway analysis and mapping may be used alone or with other position estimates to determine a final position estimate that can be used by the system or displayed to the user. In some embodiments, the image-based airway analysis and mapping systems and methods described herein may base its estimate on prior position estimates determined using a plurality of sensing modalities. Thus, higher quality and/or more reliable images may support and refine the initial and subsequent position estimation process. The image management systems and methods can complement other image processing systems and methods described herein. Identifying uninformative and/or unreliable images can allow for removal of them from further processing, thus reducing the need for subsequent processing and potentially reducing the number of unhelpful or incorrect results (e.g., due to poor image quality).

Figure 24:
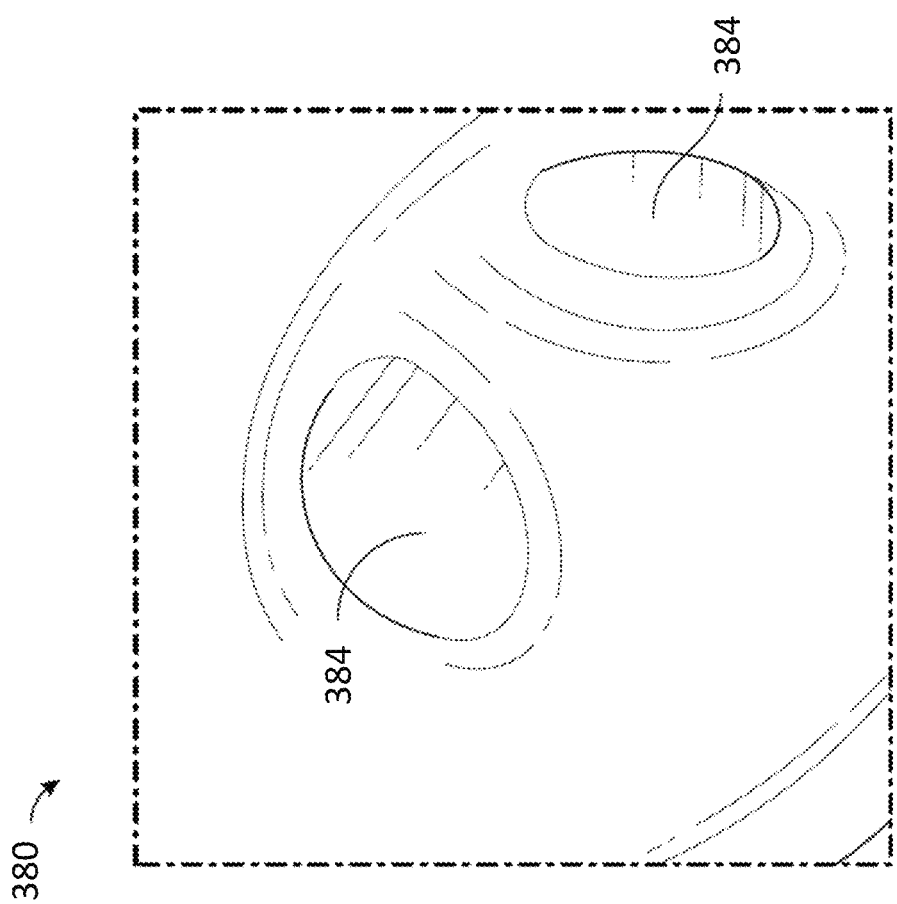
FIG. 24 provides an example image of an interior of a branch of a luminal network.

Image management may include analyzing one or more images captured by the imaging device 315 of an instrument positioned within a luminal network to detect one or more airways in the image. FIG. 24 provides an example image 380 of an interior of a branch of a luminal network. In the illustrated example, the image 380 is an interior image of an airway of a lung, although the image 380 may be representative of any type of luminal network. Two subsequent airways 384 are shown in the image 380. The airways 384 are connected to the current airway from which the image is captured.

B. Example Image Management Methods and Systems

Figure 25:
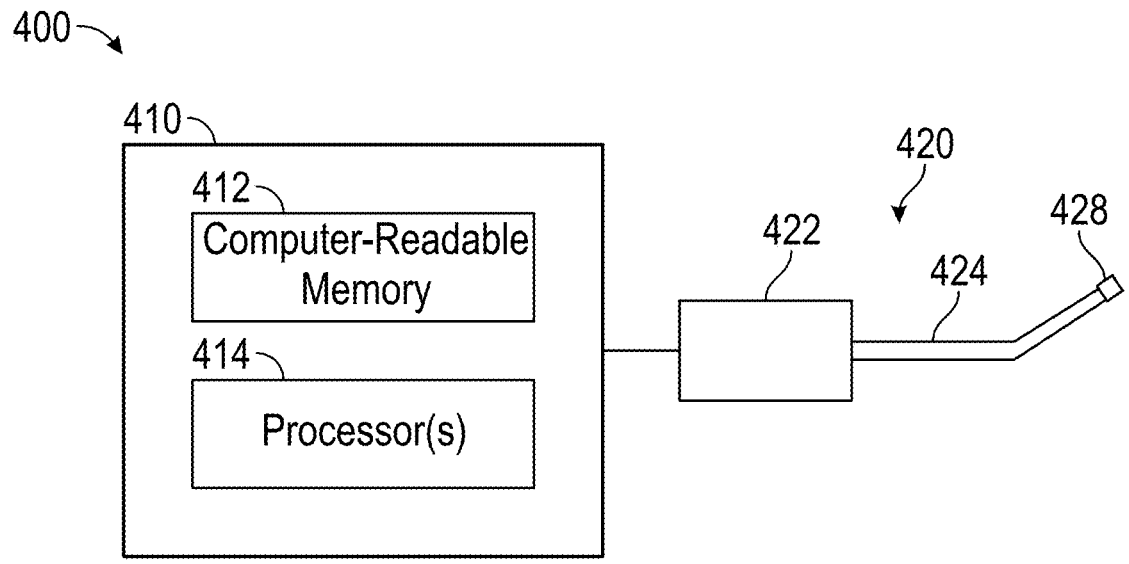
FIG. 25 shows an example image management system that includes an analysis system and a medical instrument.

By contrast to FIG. 24, some images may not be sufficiently clear or reliable (to a human and/or a computer algorithm). Thus, an image management system may be advantageously employed to identify and utilize the clear, reliable, and/or otherwise high quality images. FIG. 25 shows an example image management system 400 that includes an analysis system 410 and a medical instrument 420. The analysis system 410 may be coupled to the medical instrument. For example, the analysis system 410 may be electronically connected to the medical instrument 420. In some configurations, the analysis system 410 and the medical instrument 420 are housed within the same housing.

The analysis system 410 can include a computer-readable memory 412 and one or more processors 414. The memory 412 can be non-transitory and may include executable instructions that are configured to cause the image management system 400 to perform various functions when executed by a processor. The one or more processors 414 can be in communication with the memory 412 and may be configured to execute the instructions for performing the various functions described herein. By way of example and not limitation, the memory 412 and/or the processors 414 may be disposed in the tower 30 shown in FIG. 1, the cart 11 shown in FIGS. 1-4, the beds shown in FIGS. 5-14, etc.

The medical instrument 420 can include an instrument base 422, an elongate body 424, and/or an imaging device 428. The medical instrument 420 may share some functionality of the endoscope 116 of FIG. 21, the medical instrument 300 of FIG. 23, the endoscope 13 of FIG. 1, the ureteroscope 32 of FIG. 3, the laparoscope 59 of FIG. 9, etc.

The medical instrument 420 can include an elongate body 424 coupled to the instrument base 422. A distal end (e.g., distal tip) of the elongate body 424 can include an imaging device 428. The distal end of the elongate body 424 can additionally or alternatively include one or more illumination sources (not shown) configured to illuminate the luminal network. As with other medical instruments described herein, the distal end of the elongate body 424 can further include an opening to a working channel of the medical instrument 420 through which surgical instruments may be inserted along and/or within the instrument shaft, allowing access to the area of the luminal network near the instrument tip. The imaging device 428 may include various functionality described above with respect to the imaging device 315.

Figure 26:
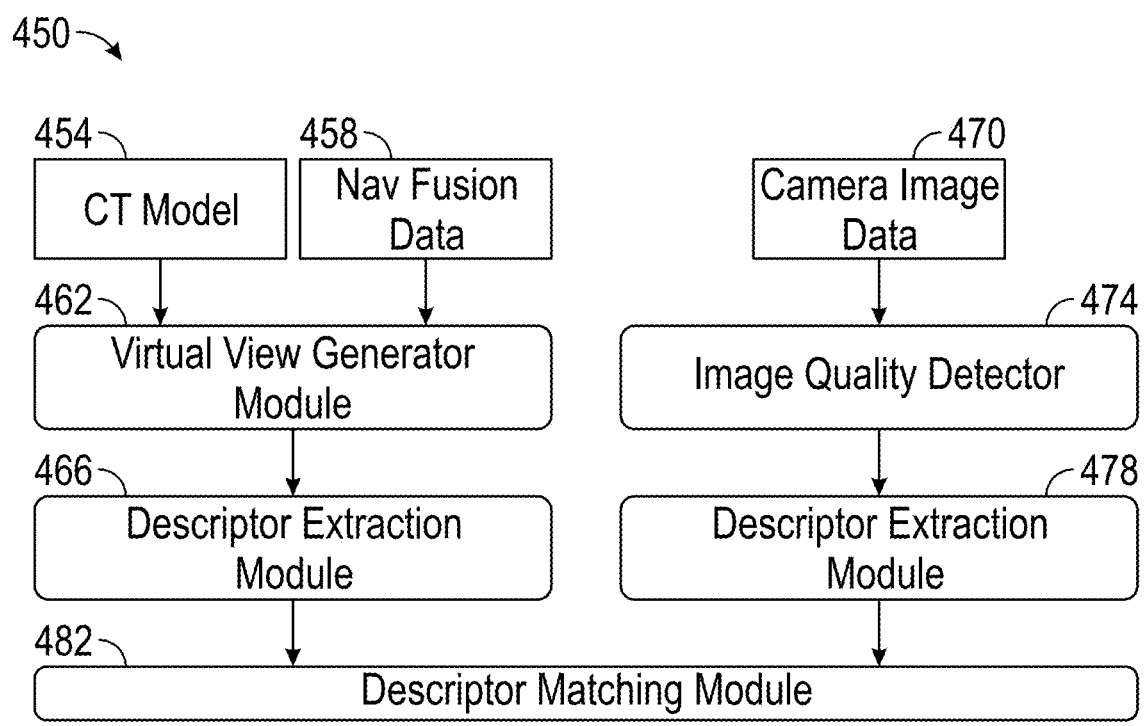
FIG. 26 shows a mapping system that can be used in combination with a medical system described herein.

FIG. 26 shows a mapping system 450 that can be used in combination with a medical system described herein. The mapping system 450 can include a virtual view generator module 462, a descriptor extraction module 466, an image quality detector 474, a descriptor extraction module 478, and/or a descriptor matching module 482. A first set of algorithms can include the virtual view generator module 462 and/or a descriptor extraction module 466, and can generate and analyze virtual (e.g., computer-generated, simulated, artificial, etc.) images that can be used in helping other algorithms identify features in image data obtained from one or more image sensors (e.g., the camera image data 470). The first set of algorithms may be applied to the CT model 454 and/or the navigation fusion data 458, e.g., before a medical procedure. Thus, output from the descriptor extraction module 466 can be stored as preoperative data.

The mapping system 450 may be configured to receive data comprising a CT model 454, navigation fusion data 458, and/or camera image data 470. The CT model 454 can include virtual images that are based on or model the CT. The CT model 454 may include a database of preoperative images that can be accessed by computer algorithms (e.g., the virtual view generator module 462, the descriptor extraction module 466, the descriptor matching module 482, etc.). The navigation fusion data 458 may include additional data, such as image data, EM data, and/or results from comparisons with camera images (e.g., the camera image data 470).

Data from the CT model 454 and/or the navigation fusion data 458 may be passed to the virtual view generator module 462. The virtual view generator module 462 can receive the data and generate a virtual model of a luminal network, e.g., a two-dimensional (2D) or three-dimensional (3D) model of the luminal network. The virtual view generator module 462 can be configured to model or mimic image views that may be obtained during a medical procedure. The generated images/model can be passed to the descriptor extraction module or algorithm 466. The descriptor extraction module 466 may be configured to receive the generated images/model and identify salient or meaningful features (e.g., descriptors) from the images. For example, the descriptor extraction module 466 can be configured to identify edges, shapes, color gradations, and/or other aspects of an image (e.g., virtual image). Additional information related to virtual model generation and analysis is further described in U.S. Patent Application Publication No. 2019/0110843, published on Apr. 18, 2019, the entirety of which is incorporated herein by reference. Data obtained from the descriptor extraction module 466 may be passed to the descriptor matching module 482, for example, so that it is available during a procedure.

A second set of algorithms can be configured to analyze camera image data 470 that can ultimately be used to compare output(s) from the first set of algorithms to identify meaningful features (e.g., descriptors) in the image data obtained from the image sensors. As noted above, through the analysis of real-time image data from a camera or other imaging device 428 at a distal tip/portion of a medical instrument 420, uninformative image data may be discarded while informative image data can be retained and used to localize the medical instrument 420 and/or help a navigate the medical instrument 420 through the luminal network. As the second set of algorithms sifts through the vast set of informative and uninformative images, whatever images are retained are used to more efficiently, quickly, and/or accurately localize the medical instrument 420. The system may rely on one or more image quality metrics (e.g., blurness, specularness, featureness, etc.), described in more detail below, to determine whether an image is uninformative and thus whether the image should be discarded. Within each image quality metric, a threshold can be set to establish a level of sensitivity in the analysis as to whether the image satisfies that image quality metric or not. Based on the results of this analysis, images may be retained for use in localization and/or navigation, or the images may be discarded to prevent distraction and/or inaccuracies in the localization of the medical instrument 420. The second set of algorithms can include an image quality detector 474, descriptor extraction module 478, and/or descriptor matching module 482. The image quality detector 474 may receive the camera image data 470 and analyze it to determine whether the camera image data 470 satisfies one or more quality metrics. Features of the image quality detector 474 are described in further detail below (e.g., with reference to FIG. 27). For example, the image quality detector 474 may be configured to identify a degree of blurness, a degree of specularness, and/or a degree of featureness related to a received image. If the image does not pass one or more threshold quality metrics based on one or more corresponding image quality metrics, then the image may be rejected and/or discarded. In some embodiments, images that pass the quality metric may be further analyzed by the descriptor extraction module 478. An image may be determined to be sufficiently reliable, informative, and/or high quality if a target number (e.g., one, two, three, four, etc.) and/or target combination of the one or more quality metrics meet the respective one or more threshold quality metrics.

The descriptor extraction module 478 can be configured to identify one or more features (e.g., descriptors) from the received images. For example, the descriptor extraction module 478 may be configured to identify a branching, a curvature, an irregularity, or other salient feature within a received image. The descriptor extraction module 478 may then pass the images and/or associated descriptor data to the descriptor matching module 482.

The descriptor matching module 482 can receive the images and/or descriptor data from the descriptor extraction module 478 and/or from the descriptor extraction module 466. The descriptor matching module 482 may identify a location of a medical instrument (e.g., an endoscope), such as described herein, within the luminal network. For example, the descriptor matching 482 can compare one or more features obtained from the descriptor extraction module 466 with features identified within the data from the descriptor extraction module 478. In some examples, the descriptor matching module 482 may include expected location data (e.g., preloaded or pre-stored into the module 482 and/or memory accessible by the module 482) to streamline a comparison of the features received from the descriptor extractions 466, 478. Thus, using the mapping system 450, a medical system can identify and/or estimate a position of the medical instrument within the luminal network based on descriptors extracted from one or more sources of data, e.g., the CT model 454, the navigation fusion data 458, and/or the camera image data 470.

Figure 27:
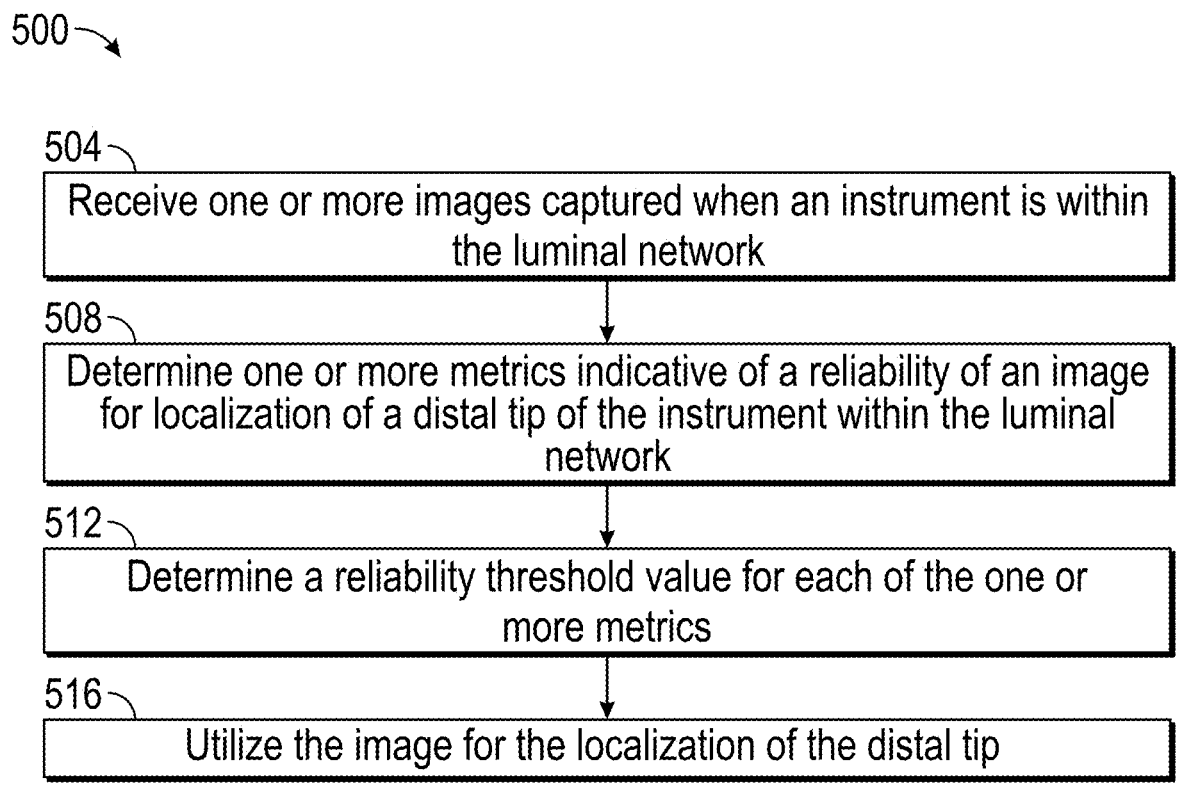
FIG. 27 illustrates an example method for implementing the image management system described above.

FIG. 27 illustrates an example method 500 for implementing the image management system described above. The method 500 can be implemented in various of the robotically-controlled systems, or component(s) thereof, described throughout this disclosure. The method 500 can be implemented with a robotic system including an instrument having an elongate body configured to be inserted into a luminal network. An imaging device can be positioned on the elongate body (e.g., on a distal end of the elongate body). The instrument can be attached to an instrument positioning device (e.g., a robotic arm) configured to move the instrument through the luminal network. A system employing the method 500 can include a processor configured with instructions that cause a processor to execute the method 500. The method 500 is provided by way of example only and the image management method can be implemented using different steps than those shown in FIG. 27. For simplicity, the steps illustrated in FIG. 27 are described as being performed by a system (e.g., one of the systems described herein or a system configured to perform one or more of the techniques described here), though the steps may be performed by one or more components or processor of such a system.

At block 504, the system for image management receives from a device (e.g., the imaging device 428) one or more images captured when the elongate body is within the luminal network. At block 508, the system determines, for each of the one or more images, one or more quality metrics that are indicative of a reliability of an image for localization of the distal tip or portion of the elongate body within the luminal network. Examples of quality metrics are provided below. At block 512, the system determines a reliability threshold value for each of the one or more quality metrics. The reliability threshold value can be supplied by a user and/or may be determined based on the quality metrics and/or the values of the quality metrics. For example, a threshold may be set relatively high for an important quality metric but may be set lower for a quality metric that is less important. Other configurations are possible. At block 516, in response to each of the one or more metrics for the image meeting a corresponding reliability threshold value, the system utilizes the image for the location of the distal tip. The system may use the image to determine a location of the distal tip of the instrument. The location determination may be based in part on the algorithms described with respect to FIG. 26 and/or other algorithms described herein (e.g., with respect to FIG. 20). It is noted that the system may discard or otherwise not utilize the image for determining the location of the distal tip of the instrument in response to one or more of the quality metrics for the image not meeting a corresponding reliability threshold value.

In some examples, the system accesses preoperative model data. The system may, for example, access a machine learning model of images that meet one or more reliability threshold values. Additionally or alternatively, the machine learning model may include a model of images that fail one or more reliability threshold values. Based on the machine learning model, the system may determine whether the one or more metrics for each of the one or more captured images meet the corresponding reliability threshold values. The preoperative model data may include other data, such as data (e.g., image data) indicative of an expected position of the medical device within the luminal system (e.g., using count of airways and/or landmarks corresponding to a location of the medical instrument). For example, although not illustrated in FIG. 27, the system may access a position state estimate for the instrument positioned within the luminal network. The position state estimate can include an identification of which branch the instrument is currently positioned. The position state may be based on image data that was obtained through a CT scan. Based on the position state estimate and the preoperative model data (e.g., machine learning model, CT images), the system may determine a location of the medical instrument. The position state estimate can be determined, for example, by the navigation and localization system 90 of FIG. 20. The position state estimate can be determined based on various and/or multiple position sensing modalities and information, such as preoperative model data 91, vision data 92, EM data 93 (or other position sensing data), and/or robotic command and kinematics data 94. Additional information related to position determination and mapping of pathways using preoperative model data is further described in U.S. Patent Application Publication No. 2019/0110843, published on Apr. 18, 2019, the entirety of which is incorporated herein by reference.

The system may use a plurality of image quality metrics to identify whether an image is reliable, informative, and/or otherwise sufficiently high quality. For example, three or more quality metrics may be used. For each image, the system can convert the 2D image into a collection of image locations within the image. The image locations may correspond to pixels within the image. The pixels may be arranged in a grid along two axes. The image locations may be defined as $\{I(x, y)\}_{x=1, y=1}^{W, H}$ where I(x, y) represents the data stored at an image location (x, y), and W and H denote the width and height of the image, respectively. The data stored for an image location may be stored as a vector that includes a plurality of elements. For example, I(x, y) may store the values of red, green and blue channels in an RGB image. "Channels" may refer to a type of variable that is stored by an image location. For example, an RGB image has three channels whereas a gray-scale image has one channel.

The image quality metrics can relate to variety of metrics. One factor may relate to an extent to which the image or features therein are blurry, which may be referred to as blurness or blurriness. Another factor may relate to how saturated and/or washed out an image appears. In particular, the factor may be related to the specular highlights caused by the reflection of the light (e.g., from a light source) to the camera. This factor may be referred to as specularness. Yet another factor may relate to how the salience of visual features within the image, which may be referred to as featureness. The salience of visual features may be related to the number of visual features detected within the image.

Blurness may be obtained in a variety of ways. For example, the system may convert the input RGB image into a gray-scale image. Thus, the image may vary based on a single channel, such as a degree of blackness or darkness. The system may determine a variance of nearby and/or adjacent points on the images. The variance may be obtained by performing a Laplacian operator on the vectors associated with each image location. The Laplacian operator can result in a matrix $\{L(x, y)\}_{x=1, y=1}^{W, H}$. The variance $\mu$ of the matrix may be calculated. From this, the blurness $\theta$ can be calculated using $$\theta = 1 - \frac{\sqrt{\mu}}{a},$$

where $\alpha$ is the upper limit of $\sqrt{\mu}$.

Specularness may be obtained by finding a ratio of points within the image that have specular highlight compared to the image as a whole. Thus, specularness can be the ratio or fraction of specular highlight area within an image. Specularness may be related to a saturation and/or value of each point within an image. "Saturation" may generally refer to the colorfulness of a point relative to the brightness of a similarly illuminate white. "Value" may refer to a degree of variation in a perception of a color. Specularness may be obtained by determining a number of points (e.g., pixels) that satisfy one or more thresholds. For example, specular points may refer to points that have a saturation below a threshold saturation level and/or have a value above a threshold value level.

Determining specularness for an image may include converting the image into a different type of image. The conversion may include converting a multi-channel image into a different type of multi-channel image (e.g., an HSV image). For example, an RGB image may be converted to an HSV image. In some embodiments, the R, G, B channel values may range from 0 to 1 and may be converted according to the following formulas:

$$C_{max} = \max(R, G, B)$$
$$C_{min} = \min(R, G, B)$$
$$\delta = C_{max} - C_{min}$$

$$H = \begin{cases} 0°, & \delta = 0 \\ 60° \times \left(\frac{G-B}{\delta} \mod 6\right), & C_{max} = R \\ 60° \times \left(\frac{B-R}{\delta} + 2\right), & C_{max} = G \\ 60° \times \left(\frac{B-R}{\delta} + 4\right), & C_{max} = B \end{cases}$$

$$S = \begin{cases} 0, & C_{max} = 0 \\ \frac{\delta}{C_{max}}, & C_{max} \neq 0 \end{cases}$$

$$V = C_{max}$$

The acronym HSV stands for Hue, Saturation and Value. Each location of the image may be analyzed for its level of specular highlight. A saturation threshold $\sigma_{Sat}$ and/or a value threshold $\sigma_{Val}$ may be set to identify the points (e.g., pixels) that have sufficient specular highlight. For example, a pixel may be identified as having sufficient specular highlight if the pixel both (1) has a saturation amount below the saturation threshold $\sigma_{Sat}$ and (2) has a value amount below the value threshold $\sigma_{Val}$. Based on a total number of points (e.g., pixels) having sufficient specular highlight, a ratio can be obtained by calculating $$\varphi = \frac{\sum_{i=1, j=1}^{W, H} \omega_{i,j}}{W \cdot H},$$

where $\omega_{i,j}=1$ if the point has saturation amount lower than $\sigma_{Sat}$ and value amount higher than $\sigma_{Val}$. Otherwise, $\omega_{i,j}=0$. The specularness of the photo may include the ratio that is obtained.

The featureness may be determined by identifying a number of features within a particular image. The number of features may be determined using one or more feature detection algorithms, such as scale-invariant feature transform (SIFT), speeded up robust features (SURF), binary robust independent elementary features (BRIEF), features from accelerated segment test (FAST), oriented FAST and rotated BRIEF (ORB), and/or binary robust invariant scalable keypoints (BRISK). In some implementations, a Harris algorithm (e.g., the Harris affine region detector) may be used to identify aspects of features, such as corners, in the image. For example, a Gaussian kernel filtering may be used on one or more scales and/or may further include localizing the salient features (e.g., corners, edges, blobs, ridges, etc.). Additionally or alternatively, a filter, such as a Sobel filter (e.g., using a Sobel operator), can be used to help identify and/or detect aspects of features, such as edges. The features may be cross-sections of a luminal network, irregularities in a lumen or branch, or some other feature of interest. Features in the images may include edges, corners, and/or other distinguishable elements in the environment. Thus, such aspects may be identified to determine the existence of a feature in the image.

As noted above, one or more quality metrics may be used to identify an image that is reliable and/or informative. In some configurations, the method 500 can include using a combination (e.g., linear combination) of the quality metrics described above. For example, an image may be classified as uninformative and/or unreliable if (1) the blurness θ is greater than a blurness threshold $\sigma_{blur}$, (2) the specularness φ is greater than a specularness threshold $\sigma_{spec}$, and/or (3) the featureness δ is less than a featureness threshold $\sigma_{feat}$. Thus, for example, in some implementations, an image is determined to be unreliable if θ>$\sigma_{blur}$, φ>$\sigma_{spec}$, and δ<$\sigma_{feat}$. In some configurations, the image may determined to be unreliable if a linear combination of the quality metrics results in a composite metric that is below a composite threshold. The composite metric ρ may be determined using one or more weighting factors that correspond to respective quality metrics. The weighting factors may be linear weighting factors, though other variations are possible. For example, the composite metric ρ may be determined using $\rho = \alpha \cdot \theta + \beta \cdot \varphi + \gamma \cdot$ $$\left(1 - \frac{\delta}{b}\right).$$

Here, α, β, and γ represent respective weighting parameters for each quality metric (e.g., blurness θ, specularness φ, featureness δ). In some implementations, an limit value b can represent an upper limit of the number of features that is detected in an endoscopic image. The weighting parameters may be selected based on an analysis of a set of representative images. Thus, the weighting parameters may be included in the preoperative data described herein.

As noted above, in some configurations, the system may additionally or alternatively implement a machine learning (ML) algorithm to determine one or more of the quality metrics described above. The machine learning algorithm can be configured to capture holistic information of an image additionally or alternatively to granular (e.g., pixel-level) image data. The ML algorithm can be configured to identify reliable and/or informative images. Additionally or alternatively, the ML algorithm can be configured to identify unreliable and/or uninformative images.

The ML algorithm may be previously trained on "good" (e.g., informative, reliable) and/or "bad" (e.g., uninformative, unreliable) images. The training algorithm may use classifiers such as Random Forests, Support Vector Machines or Convolutional Neural Networks (CNNs). Thus, "good" and/or "bad" images may be determined based on the trained classifiers.

Once trained, the ML algorithm or model can be stored in the system (e.g., the memory 412). Some examples of machine learning algorithms include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms.

As noted above, the method 500 can include accessing the machine learning model and using the model to determine whether the quality metric(s) for each image meets the corresponding reliability threshold value(s). The machine learning model can include a convolutional neural network that is trained to identify branchings within the one or more luminal networks. The machine learning model can be based at least in part on simulated imagery of the luminal network. For example, the simulated imagery can include at least one computer-generated image of the luminal network over two or three dimensions. For example, the machine learning model may be based at least in part on images collected from a CT scan. The simulated imagery may depict a simulated perspective from within the luminal network. Additionally or alternatively, the image data may include video imagery (e.g., from a bronchial network within a patient).

The ML algorithm may be trained in a number of ways. For example, the system may access a 3D representation of a luminal network. The system may access one or more images of an interior of the luminal network. In some configurations, the system may determine, based on the images of the interior of the luminal network and the 3D representation of the luminal network, a mapping between each image and a corresponding location within the 3D representation. The system may set weighting parameters, based on the mapping, to identify, within image data presented to the ML algorithm, a corresponding branching of the luminal network and/or a location of the corresponding branching within the luminal network. Additionally or alternatively, the system can predict, based on a particle filter, one or more features within the image.

IV. Implementing Systems and Terminology

Implementations disclosed herein provide systems, methods and apparatus for image management for navigation robotically-controlled medical instruments. Various implementations described herein provide for improved image management and navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The image data, analysis and/or management algorithms, machine learning model(s), position estimation, and/or robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A system comprising:
    an instrument comprising:
        an elongate body configured to be inserted into a luminal network, and an imaging device positioned at a distal tip of the elongate body;
    at least one non-transitory computer-readable storage medium having stored thereon executable instructions; and
    one or more processors in communication with the at least one non-transitory computer-readable storage medium and configured to execute the executable instructions to cause the system to at least:
        receive, from the imaging device, a plurality of images captured when the elongate body is within the luminal network;
        for each of the plurality images, determine one or more metrics indicative of image reliability for localization of the distal tip of the elongate body within the luminal network, wherein the one or more metrics comprise at least one of: a first metric indicative of a level of blurriness in the respective image; a second metric indicative of an amount of specular highlights in the respective image; or a third metric indicative of an availability of visual features in the respective image;
        determine a reliability threshold value for each of the one or more metrics;
        in response to at least one of the one or more metrics not meeting a corresponding reliability threshold value for a first image of the plurality of images, automatically discard the first image; and
        in response to each of the one or more metrics meeting a corresponding reliability threshold value for a second image of the plurality of images, utilize the second image for the localization of the distal tip.

2. The system of claim 1, wherein the one or more processors are configured to execute the executable instructions to cause the system to at least:
    access a machine learning model of images meeting one or more reliability threshold values; and
    determine, based on the machine learning model, whether the one or more metrics for each of the plurality of images meet the corresponding reliability threshold values.

3. The system of claim 2, wherein the machine learning model comprises a convolutional neural network trained to differentiate between (i) images with one or more metrics that meet the corresponding reliability threshold values and (ii) images with one or more metrics that do not meet the corresponding reliability threshold values.

4. The system of claim 1, wherein the utilizing of the second image comprises:
    assigning a first weighting parameter to the first metric;
    assigning a second weighting parameter to the second metric;
    assigning a third weighting parameter to the third metric; and
    determining a composite metric based on a linear combination of the first, second, and third metrics with the respective first, second, and third weighting parameters; wherein the composite metric is indicative of a reliability of the second image for the localization of the distal tip.

5. The system of claim 1, wherein said determining the one or more metrics comprises identifying image values corresponding to two-dimensional coordinates of the respective image, wherein each image value of the image values is based on color values at the corresponding coordinate.

6. The system of claim 1, wherein said determining the one or more metrics comprises determining the first metric based on: performing a Laplacian operator on a modified image of the respective image to obtain a matrix; and determining a variance of the matrix associated with the modified image.

7. The system of claim 1, wherein said determining the one or more metrics comprises determining the second metric based on: determining saturation and lightness values for the respective image; and determining a ratio of at least one of saturation or value to an area of the respective image.

8. The system of claim 7, wherein determining the second metric comprises determining a variance of lightness values between a first point and a second point of the respective image, the first and second points being adjacent to each other.

9. The system of claim 7, wherein determining the second metric comprises identifying a number of pixels that have saturation values below a threshold saturation level.

10. The system of claim 1, wherein said determining the one or more metrics comprises determining the third metric based on using at least one of scale-invariant feature transform (SIFT), speeded up robust features (SURF), binary robust independent elementary features (BRIEF), binary robust invariant scalable keypoints (BRISK), or features from accelerated segment test (FAST) to identify a number of features in the respective image.

11. The system of claim 1, wherein the one or more processors are further configured to execute the executable instructions to cause the system to identify at least one of an edge or a corner in the second image.

12. The system of claim 1, wherein the one or more processors are further configured to execute the executable instructions to cause the system to assign a reliability factor to each of the plurality of images, the reliability factor based on the one or more metrics and indicative of a reliability of the respective images for localization of the distal tip.

13. The system of claim 1, wherein the one or more processors are further configured to execute the executable instructions to cause the system to receive from a user each of the reliability threshold values corresponding to the one or more metrics.

14. The system of claim 1, wherein the one or more processors are further configured to execute the executable instructions to cause the system to automatically set a first reliability threshold value higher than a second reliability threshold value based on corresponding first and second metrics of the one or more metrics.

15. The system of claim 1, wherein the one or more processors are further configured to execute the executable instructions to cause the system to access preoperative model data comprising virtual images.

16. The system of claim 15, wherein accessing preoperative model data comprises comparing the plurality of images captured when the elongate body is within the luminal network with the virtual images.

17. The system of claim 16, wherein the one or more processors are further configured to execute the executable instructions to cause the system to determine a location of the elongate body within the luminal network based on comparing the plurality of images captured when the elongate body is within the luminal network with the virtual images.

18. A method comprising:
receiving, from an image device disposed at a distal end of an elongate instrument, a plurality of images captured when the elongate instrument is within a luminal network;
accessing a machine learning model trained on images meeting one or more threshold quality metrics,
wherein the one or more threshold quality metrics comprise at least one of:
a first metric indicative of a level of blurriness in the respective image;
a second metric indicative of an amount of specular highlights in the respective image; or
a third metric indicative of an availability of visual features in the respective image;
determining, based on the machine learning model, that a first image of the plurality of images does not meet at least one of the one or more threshold quality metrics;
automatically labeling the first image as uninformative based on the determination that the first image does not meet the at least one of the one or more threshold quality metrics;
determining, based on the machine learning model, that a second image of the plurality of images meets the one or more threshold quality metrics; and
determining a location of the distal end of the elongate instrument using the second image based on the determination that the second image meets the one or more threshold quality metrics.

19. The method of claim 18, further comprising setting threshold levels for the one or more threshold quality metrics.

20. The method of claim 18, further comprising determining the one or more threshold quality metrics.

21. The method of claim 18, further comprising filtering the first image from being used for the determination of the location of the distal end in response to the determination that the first image does not meet the at least one of the one or more quality metrics.

22. The method of claim 18, further comprising identifying the second image as a relatively high quality image based on the determination that the second image meets the one or more threshold quality metrics.

23. The method of claim 18, wherein said determining the location of the distal end of the elongate instrument within the luminal network comprises comparing the plurality of images with preoperative images of a luminal network.

24. The method of claim 23, wherein the preoperative images comprise computer-generated images.

25. The method of claim 23, wherein the preoperative images comprise images obtained from a computerized tomography (CT) scan.

26. A system comprising:
an instrument comprising:
an elongate body configured to be inserted into a luminal network, and an imaging device associated with a distal tip of the elongate body;
at least one non-transitory computer-readable storage medium having stored thereon executable instructions; and
one or more processors in communication with the at least one non-transitory computer-readable storage medium memory and configured to execute the executable instructions to cause the system to at least:
receive, from the imaging device, a plurality of images captured when the elongate body is within the luminal network;
for each of the one or more plurality of images, determine one or more metrics indicative of a reliability of the respective image for localization of the distal tip of the elongate body within the luminal network, wherein the one or more metrics comprise at least one of: a first metric indicative of a level of blurriness in the respective image; a second metric indicative of an amount of specular highlights in the respective image; or a third metric indicative of an availability of visual features in the respective image;
determine a reliability threshold value for each of the one or more metrics;

in response to at least one of the one or metrics of a first image of the plurality of images not meeting a corresponding reliability threshold value, not utilizing the first image in determining a location of the distal tip of the elongate body; and in response to at least one of the one or more metrics of a second image meeting the corresponding reliability threshold value, utilize the second image in determining the location of the distal tip of the elongate body.

27. A system comprising:

an instrument comprising:
an elongate body configured to be inserted into a luminal network, and an imaging device positioned at a distal tip of the elongate body;
at least one non-transitory computer-readable storage medium having stored thereon executable instructions; and
one or more processors in communication with the at least one non-transitory computer-readable storage medium and configured to execute the executable instructions to cause the system to at least:
receive, from the imaging device, a plurality of images captured when the elongate body is within the luminal network;
for each of the plurality of images, determine one or more metrics indicative of image reliability for localization of the distal tip of the elongate body within the luminal network, wherein the one or more metrics comprise at least one of: a first metric indicative of a level of blurriness in the respective image; a second metric indicative of an amount of specular highlights in the respective image; or a third metric indicative of an availability of visual features in the respective image;
automatically discard a first image of the plurality of images based at least in part on the one or more metrics associated with the first image; and
utilize a second image of the plurality of images for the localization of the distal tip based at least in part on the one or more metrics associated with the second image; and
access a machine learning model of images meeting one or more reliability threshold values; and determine, based on the machine learning model, whether the one or more metrics for each of the plurality of images meet respective corresponding reliability threshold values of the one or more reliability threshold values.

28. The system of claim 27, wherein the utilizing of the second image comprises:
assigning a first weighting parameter to the first metric;
assigning a second weighting parameter to the second metric;
assigning a third weighting parameter to the third metric; and
determining a composite metric based on a combination of the first, second, and third metrics with the respective first, second, and third weighting parameters;
wherein the composite metric is indicative of a reliability of the second image for the localization of the distal tip.

29. The system of claim 27, wherein said determining the one or more metrics for each of the plurality of images comprises determining at least one metric based on:
performing a Laplacian operator on a modified image of the respective image to obtain a matrix; and
determining a variance of the matrix associated with the modified image.

30. The system of claim 27, wherein said determining the one or more metrics for each of the plurality of images comprises determining at least one metric based on:
determining saturation and lightness values for the respective image; and
determining a ratio of at least one of saturation or value to an area of the respective image.

31. The system of claim 27, wherein said determining the one or more metrics for each of the plurality of images comprises determining at least one metric using at least one of scale-invariant feature transform (SIFT), speeded up robust features (SURF), binary robust independent elementary features (BRIEF), binary robust invariant scalable keypoints (BRISK), or features from accelerated segment test (FAST) to identify a number of features in the respective image.

* * * * *